United States Patent
Avitall et al.

(10) Patent No.: US 9,757,191 B2
(45) Date of Patent: *Sep. 12, 2017

(54) ELECTROPHYSIOLOGY SYSTEM AND METHODS

(71) Applicant: Boston Scientific Scimed Inc., Maple Grove, MN (US)

(72) Inventors: Boaz Avitall, Whitefish Bay, WI (US); Josef V. Koblish, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 84 days.

This patent is subject to a terminal disclaimer.

(21) Appl. No.: 14/498,211

(22) Filed: Sep. 26, 2014

(65) Prior Publication Data
US 2015/0011995 A1    Jan. 8, 2015

Related U.S. Application Data

(63) Continuation of application No. 13/738,562, filed on Jan. 10, 2013, now Pat. No. 8,876,817.
(Continued)

(51) Int. Cl.
*A61B 18/12* (2006.01)
*A61B 18/14* (2006.01)
(Continued)

(52) U.S. Cl.
CPC ........ *A61B 18/1492* (2013.01); *A61B 5/0422* (2013.01); *A61B 5/6852* (2013.01);
(Continued)

(58) Field of Classification Search
CPC . A61B 18/1206; A61B 18/1492; A61B 18/18; A61B 2018/0016;
(Continued)

(56) References Cited

U.S. PATENT DOCUMENTS 3,773,401 A    11/1973 Douklias et al.
4,466,443 A    8/1984 Utsugi
(Continued)

FOREIGN PATENT DOCUMENTS

CA    2682055 A1    10/2008
CA    2847846 A1    3/2013
(Continued)

OTHER PUBLICATIONS

Goldberg, S. Nahum et al., "Variables Affecting Proper System Grounding for Radiofrequency Ablation in an Animal Model", JVIR, vol. 11, No. 8, Sep. 2000, pp. 1069-1075.
(Continued)

*Primary Examiner* — Daniel Fowler
(74) *Attorney, Agent, or Firm* — Faegre Baker Daniels LLP

(57) ABSTRACT

An electrophysiology system comprises an ablation catheter, a radiofrequency generator, and a mapping processor. The ablation catheter has a tissue ablation electrode and a plurality of microelectrodes distributed about the circumference of the tissue ablation electrode and electrically isolated therefrom. The plurality of microelectrodes define a plurality of bipolar microelectrode pairs. The mapping processor is configured to acquire output signals from the bipolar microelectrode pairs, compare the output signals, and generate an output to a display providing a visual indication of a characteristic of the microelectrodes and the tissue ablation electrode relative to myocardial tissue to be mapped and/or ablated.

13 Claims, 14 Drawing Sheets

Related U.S. Application Data

(60) Provisional application No. 61/585,083, filed on Jan. 10, 2012, provisional application No. 61/715,032, filed on Oct. 17, 2012.

(51) Int. Cl.
*A61B 18/18* (2006.01)
*A61B 5/042* (2006.01)
*A61B 5/00* (2006.01)
*A61B 18/00* (2006.01)
*A61B 5/0464* (2006.01)
*A61B 5/06* (2006.01)

(52) U.S. Cl.
CPC .......... *A61B 18/1206* (2013.01); *A61B 18/18* (2013.01); *A61B 5/0464* (2013.01); *A61B 5/065* (2013.01); *A61B 5/4887* (2013.01); *A61B 2018/0016* (2013.01); *A61B 2018/00357* (2013.01); *A61B 2018/00577* (2013.01); *A61B 2018/00642* (2013.01); *A61B 2018/00654* (2013.01); *A61B 2018/00678* (2013.01); *A61B 2018/00839* (2013.01); *A61B 2018/00898* (2013.01); *A61B 2018/00904* (2013.01); *A61B 2018/00916* (2013.01); *A61B 2018/126* (2013.01); *A61B 2218/002* (2013.01)

(58) Field of Classification Search
CPC  A61B 2018/00351; A61B 2018/00577; A61B 2018/00642; A61B 2018/00654; A61B 2018/00678; A61B 2018/00839; A61B 2018/00898; A61B 2018/00904; A61B 2018/00916; A61B 2018/126; A61B 2218/002; A61B 5/0422; A61B 5/0464; A61B 5/065; A61B 5/4887; A61B 5/6852
See application file for complete search history.

(56) References Cited

U.S. PATENT DOCUMENTS

| | | |
|---|---|---|
| 4,602,624 A | 7/1986 | Naples et al. |
| 4,633,882 A | 1/1987 | Matsuo et al. |
| 4,732,149 A | 3/1988 | Sutter |
| 4,763,660 A | 8/1988 | Kroll et al. |
| 4,966,145 A | 10/1990 | Kikumoto et al. |
| 5,019,076 A | 5/1991 | Yamanashi et al. |
| 5,029,588 A | 7/1991 | Yock et al. |
| 5,178,150 A | 1/1993 | Silverstein et al. |
| 5,217,460 A | 6/1993 | Knoepfler |
| 5,238,004 A | 8/1993 | Sahatjian et al. |
| 5,240,003 A | 8/1993 | Lancee et al. |
| 5,254,088 A | 10/1993 | Lundquist et al. |
| 5,295,482 A | 3/1994 | Clare et al. |
| 5,318,589 A | 6/1994 | Lichtman |
| 5,324,284 A | 6/1994 | Imran |
| 5,331,966 A | 7/1994 | Bennett et al. |
| 5,334,193 A | 8/1994 | Nardella |
| 5,341,807 A | 8/1994 | Nardella |
| 5,377,685 A | 1/1995 | Kazi et al. |
| 5,383,874 A | 1/1995 | Jackson et al. |
| 5,385,146 A | 1/1995 | Goldreyer |
| 5,385,148 A | 1/1995 | Lesh et al. |
| 5,391,199 A | 2/1995 | Ben-Haim |
| 5,398,683 A | 3/1995 | Edwards et al. |
| 5,423,811 A | 6/1995 | Imran et al. |
| 5,447,529 A | 9/1995 | Marchlinski et al. |
| 5,462,521 A | 10/1995 | Brucker et al. |
| 5,482,054 A | 1/1996 | Slater et al. |
| 5,485,849 A | 1/1996 | Panescu et al. |
| 5,494,042 A | 2/1996 | Panescu et al. |
| 5,500,012 A | 3/1996 | Brucker et al. |
| 5,520,683 A | 5/1996 | Subramaniam et al. |
| 5,571,088 A | 11/1996 | Lennox et al. |
| 5,573,535 A | 11/1996 | Viklund |
| 5,575,772 A | 11/1996 | Lennox |
| 5,579,764 A | 12/1996 | Goldreyer |
| 5,582,609 A | 12/1996 | Swanson et al. |
| 5,647,870 A | 7/1997 | Kordis et al. |
| 5,718,701 A | 2/1998 | Shai et al. |
| 5,722,402 A | 3/1998 | Swanson et al. |
| 5,762,067 A | 6/1998 | Dunham et al. |
| 5,788,636 A | 8/1998 | Curley |
| 5,792,064 A | 8/1998 | Panescu et al. |
| 5,800,482 A | 9/1998 | Pomeranz et al. |
| 5,820,568 A | 10/1998 | Willis |
| 5,830,213 A | 11/1998 | Panescu et al. |
| 5,833,621 A | 11/1998 | Panescu et al. |
| 5,836,990 A | 11/1998 | Li |
| 5,868,735 A | 2/1999 | Lafontaine |
| 5,871,483 A | 2/1999 | Jackson et al. |
| 5,871,526 A | 2/1999 | Gibbs et al. |
| 5,876,336 A | 3/1999 | Swanson et al. |
| 5,885,278 A | 3/1999 | Fleischman |
| 5,913,856 A | 6/1999 | Chia et al. |
| 5,916,213 A | 6/1999 | Haissaguerre et al. |
| 5,957,850 A | 9/1999 | Marian et al. |
| 6,004,269 A | 12/1999 | Crowley et al. |
| 6,027,500 A | 2/2000 | Buckles et al. |
| 6,050,267 A | 4/2000 | Nardella et al. |
| 6,050,994 A | 4/2000 | Sherman |
| 6,059,778 A | 5/2000 | Sherman |
| 6,063,078 A | 5/2000 | Wittkampf |
| 6,064,905 A | 5/2000 | Webster, Jr. et al. |
| 6,068,629 A | 5/2000 | Haissaguerre et al. |
| 6,070,094 A | 5/2000 | Swanson et al. |
| 6,083,170 A | 7/2000 | Ben-Haim |
| 6,083,222 A | 7/2000 | Klein et al. |
| 6,099,524 A | 8/2000 | Lipson et al. |
| 6,101,409 A | 8/2000 | Swanson et al. |
| 6,116,027 A | 9/2000 | Smith et al. |
| 6,120,476 A | 9/2000 | Fung et al. |
| 6,165,123 A | 12/2000 | Thompson |
| 6,171,305 B1 | 1/2001 | Sherman |
| 6,200,314 B1 | 3/2001 | Sherman |
| 6,206,831 B1 | 3/2001 | Suorsa et al. |
| 6,210,337 B1 | 4/2001 | Dunham et al. |
| 6,216,027 B1 | 4/2001 | Willis et al. |
| 6,224,557 B1 | 5/2001 | Ziel et al. |
| 6,233,491 B1 | 5/2001 | Kordis et al. |
| 6,241,754 B1 | 6/2001 | Swanson et al. |
| 6,270,493 B1 | 8/2001 | Lalonde et al. |
| 6,290,697 B1 | 9/2001 | Tu et al. |
| 6,352,534 B1 | 3/2002 | Paddock et al. |
| 6,395,325 B1 | 5/2002 | Hedge et al. |
| 6,400,981 B1 | 6/2002 | Govari |
| 6,423,002 B1 | 7/2002 | Hossack |
| 6,475,213 B1 | 11/2002 | Whayne et al. |
| 6,488,678 B2 | 12/2002 | Sherman |
| 6,491,710 B2 | 12/2002 | Satake |
| 6,508,767 B2 | 1/2003 | Burns et al. |
| 6,508,769 B2 | 1/2003 | Bonnefous |
| 6,508,803 B1 | 1/2003 | Horikawa et al. |
| 6,516,667 B1 | 2/2003 | Broad et al. |
| 6,517,533 B1 | 2/2003 | Swaminathan |
| 6,517,534 B1 | 2/2003 | McGovern et al. |
| 6,537,271 B1 | 3/2003 | Murray et al. |
| 6,544,175 B1 | 4/2003 | Newman |
| 6,546,270 B1 | 4/2003 | Goldin et al. |
| 6,547,788 B1 | 4/2003 | Maguire et al. |
| 6,569,160 B1 | 5/2003 | Goldin et al. |
| 6,572,547 B2 | 6/2003 | Miller et al. |
| 6,575,966 B2 | 6/2003 | Lane et al. |
| 6,575,969 B1 | 6/2003 | Rittman, III et al. |
| 6,579,278 B1 | 6/2003 | Bencini |
| 6,582,372 B2 | 6/2003 | Poland |
| 6,584,345 B2 | 6/2003 | Govari |
| 6,589,182 B1 | 7/2003 | Loftman et al. |
| 6,592,525 B2 | 7/2003 | Miller et al. |
| 6,602,242 B1 | 8/2003 | Fung et al. |
| 6,620,103 B1 | 9/2003 | Bruce et al. |
| 6,632,179 B2 | 10/2003 | Wilson et al. |
| 6,638,222 B2 | 10/2003 | Chandrasekaran et al. |

(56) References Cited

U.S. PATENT DOCUMENTS

| | | |
|---|---|---|
| 6,640,120 B1 | 10/2003 | Swanson et al. |
| 6,647,281 B2 | 11/2003 | Morency |
| 6,656,174 B1 | 12/2003 | Hegde et al. |
| 6,658,279 B2 | 12/2003 | Swanson et al. |
| 6,663,573 B2 | 12/2003 | Goldin |
| 6,666,862 B2 | 12/2003 | Jain et al. |
| 6,676,606 B2 | 1/2004 | Simpson et al. |
| 6,692,441 B1 | 2/2004 | Poland et al. |
| 6,705,992 B2 | 3/2004 | Gatzke |
| 6,709,396 B2 | 3/2004 | Flesch et al. |
| 6,711,429 B1 | 3/2004 | Gilboa et al. |
| 6,719,756 B1 | 4/2004 | Muntermann |
| 6,735,465 B2 | 5/2004 | Panescu |
| 6,736,814 B2 | 5/2004 | Manna et al. |
| 6,743,174 B2 | 6/2004 | Ng et al. |
| 6,773,402 B2 | 8/2004 | Govari et al. |
| 6,776,758 B2 | 8/2004 | Peszynski et al. |
| 6,796,979 B2 | 9/2004 | Lentz |
| 6,796,980 B2 | 9/2004 | Hall |
| 6,804,545 B2 | 10/2004 | Fuimaono et al. |
| 6,811,550 B2 | 11/2004 | Holland et al. |
| 6,824,517 B2 | 11/2004 | Salgo et al. |
| 6,837,884 B2 | 1/2005 | Woloszko |
| 6,845,257 B2 | 1/2005 | Fuimaono et al. |
| 6,845,264 B1 | 1/2005 | Skladnev et al. |
| 6,917,834 B2 | 7/2005 | Koblish et al. |
| 6,922,579 B2 | 7/2005 | Taimisto et al. |
| 6,923,808 B2 | 8/2005 | Taimisto |
| 6,932,811 B2 | 8/2005 | Hooven et al. |
| 6,945,938 B2 | 9/2005 | Grunwald |
| 6,950,689 B1 | 9/2005 | Willis et al. |
| 6,952,615 B2 | 10/2005 | Satake |
| 6,958,040 B2 | 10/2005 | Oliver et al. |
| 7,001,383 B2 | 2/2006 | Keidar |
| 7,037,264 B2 | 5/2006 | Poland |
| 7,047,068 B2 | 5/2006 | Haissaguerre |
| 7,097,643 B2 | 8/2006 | Cornelius et al. |
| 7,099,711 B2 | 8/2006 | Fuimaono et al. |
| 7,105,122 B2 | 9/2006 | Karason |
| 7,112,198 B2 | 9/2006 | Satake |
| 7,115,122 B1 | 10/2006 | Swanson et al. |
| 7,123,951 B2 | 10/2006 | Fuimaono et al. |
| 7,131,947 B2 | 11/2006 | Demers |
| 7,166,075 B2 | 1/2007 | Varghese et al. |
| 7,181,262 B2 | 2/2007 | Fuimaono et al. |
| 7,220,233 B2 | 5/2007 | Nita et al. |
| 7,232,433 B1 | 6/2007 | Schlesinger et al. |
| 7,247,155 B2 | 7/2007 | Hoey et al. |
| 7,270,634 B2 | 9/2007 | Scampini et al. |
| 7,288,088 B2 | 10/2007 | Swanson |
| 7,291,142 B2 | 11/2007 | Eberl et al. |
| 7,306,561 B2 | 12/2007 | Sathyanarayana |
| 7,335,052 B2 | 2/2008 | D'Sa |
| 7,347,820 B2 | 3/2008 | Bonnefous |
| 7,347,821 B2 | 3/2008 | Skyba et al. |
| 7,347,857 B2 | 3/2008 | Anderson et al. |
| 7,361,144 B2 | 4/2008 | Levrier et al. |
| 7,422,591 B2 | 9/2008 | Phan |
| 7,438,714 B2 | 10/2008 | Phan |
| 7,455,669 B2 | 11/2008 | Swanson |
| 7,488,289 B2 | 2/2009 | Suorsa et al. |
| 7,507,205 B2 | 3/2009 | Borovsky et al. |
| 7,519,410 B2 | 4/2009 | Taimisto et al. |
| 7,529,393 B2 | 5/2009 | Peszynski et al. |
| 7,534,207 B2 | 5/2009 | Shehada et al. |
| 7,544,164 B2 | 6/2009 | Knowles et al. |
| 7,549,988 B2 | 6/2009 | Eberl et al. |
| 7,569,052 B2 | 8/2009 | Phan et al. |
| 7,578,791 B2 | 8/2009 | Rafter |
| 7,582,083 B2 | 9/2009 | Swanson |
| 7,585,310 B2 | 9/2009 | Phan et al. |
| 7,610,073 B2 | 10/2009 | Fuimaono et al. |
| 7,648,462 B2 | 1/2010 | Jenkins et al. |
| 7,697,972 B2 | 4/2010 | Verard et al. |
| 7,704,208 B2 | 4/2010 | Thiele |
| 7,720,420 B2 | 5/2010 | Kajita |
| 7,727,231 B2 | 6/2010 | Swanson |
| 7,736,362 B2 | 6/2010 | Eberl et al. |
| 7,740,629 B2 | 6/2010 | Anderson et al. |
| 7,758,508 B1 | 7/2010 | Thiele et al. |
| 7,766,833 B2 | 8/2010 | Lee et al. |
| 7,776,033 B2 | 8/2010 | Swanson |
| 7,785,324 B2 | 8/2010 | Eberl |
| 7,794,398 B2 | 9/2010 | Salgo |
| 7,796,789 B2 | 9/2010 | Salgo et al. |
| 7,799,025 B2 | 9/2010 | Wellman |
| 7,815,572 B2 | 10/2010 | Loupas |
| 7,819,863 B2 | 10/2010 | Eggers et al. |
| 7,837,624 B1 | 11/2010 | Hossack et al. |
| 7,859,170 B2 | 12/2010 | Knowles et al. |
| 7,862,561 B2 | 1/2011 | Swanson et al. |
| 7,862,562 B2 | 1/2011 | Eberl |
| 7,879,029 B2 | 2/2011 | Jimenez |
| 7,892,228 B2 | 2/2011 | Landis et al. |
| 7,894,871 B2 | 2/2011 | Wittkampf et al. |
| 7,918,850 B2 | 4/2011 | Govari et al. |
| 7,957,817 B1 | 6/2011 | Gillespie et al. |
| 7,996,085 B2 | 8/2011 | Levin |
| 8,016,822 B2 | 9/2011 | Swanson |
| 8,048,028 B2 | 11/2011 | Horn et al. |
| 8,103,327 B2 | 1/2012 | Harlev et al. |
| 8,128,617 B2 | 3/2012 | Bencini et al. |
| 8,160,690 B2 | 4/2012 | Wilfley et al. |
| 8,162,935 B2 | 4/2012 | Paul et al. |
| 8,265,745 B2 | 9/2012 | Hauck et al. |
| 8,267,926 B2 | 9/2012 | Paul et al. |
| 8,290,578 B2 | 10/2012 | Schneider |
| 8,317,783 B2 | 11/2012 | Cao et al. |
| 8,369,922 B2 | 2/2013 | Paul et al. |
| 8,400,164 B2 | 3/2013 | Osadchy et al. |
| 8,403,925 B2 | 3/2013 | Miller et al. |
| 8,406,866 B2 | 3/2013 | Deno et al. |
| 8,414,579 B2 | 4/2013 | Kim et al. |
| 8,449,535 B2 | 5/2013 | Deno et al. |
| 8,454,538 B2 | 6/2013 | Wittkampf et al. |
| 8,454,589 B2 | 6/2013 | Deno et al. |
| 8,489,184 B2 | 7/2013 | Wilfley et al. |
| 8,579,889 B2 | 11/2013 | Bencini |
| 8,583,215 B2 | 11/2013 | Lichtenstein |
| 8,603,084 B2 | 12/2013 | Fish et al. |
| 8,603,085 B2 | 12/2013 | Jimenez |
| 8,644,950 B2 | 2/2014 | Hauck |
| 8,657,814 B2 | 2/2014 | Werneth et al. |
| 8,672,936 B2 | 3/2014 | Thao et al. |
| 8,679,109 B2 | 3/2014 | Paul et al. |
| 8,728,077 B2 | 5/2014 | Paul et al. |
| 8,740,900 B2 | 6/2014 | Kim et al. |
| 8,755,860 B2 | 6/2014 | Paul et al. |
| 8,771,343 B2 | 7/2014 | Weber et al. |
| 8,894,643 B2 | 11/2014 | Watson et al. |
| 8,906,011 B2 | 12/2014 | Gelbart et al. |
| 8,945,015 B2 | 2/2015 | Rankin et al. |
| 8,998,890 B2 | 4/2015 | Paul et al. |
| 9,089,340 B2 | 7/2015 | Hastings et al. |
| 9,125,565 B2 | 9/2015 | Hauck |
| 9,125,668 B2 | 9/2015 | Subramaniam et al. |
| 9,173,586 B2 | 11/2015 | Deno et al. |
| 9,211,156 B2 | 12/2015 | Kim et al. |
| 9,241,687 B2 | 1/2016 | McGee |
| 9,241,761 B2 | 1/2016 | Rankin et al. |
| 9,254,163 B2 | 2/2016 | Paul et al. |
| 9,271,782 B2 | 3/2016 | Paul et al. |
| 9,283,026 B2 | 3/2016 | Paul et al. |
| 9,393,072 B2 | 7/2016 | Kim et al. |
| 2001/0029371 A1 | 10/2001 | Kordis |
| 2002/0087208 A1 | 7/2002 | Koblish et al. |
| 2002/0165448 A1 | 11/2002 | Ben-Haim et al. |
| 2002/0198521 A1 | 12/2002 | Maguire |
| 2003/0013958 A1 | 1/2003 | Govari et al. |
| 2003/0088240 A1 | 5/2003 | Saadat |
| 2003/0158548 A1 | 8/2003 | Phan et al. |
| 2003/0158549 A1 | 8/2003 | Swanson |
| 2003/0229286 A1 | 12/2003 | Lenker |
| 2004/0006268 A1 | 1/2004 | Gilboa et al. |

(56) References Cited

U.S. PATENT DOCUMENTS

| | | |
|---|---|---|
| 2004/0082860 A1 | 4/2004 | Haissaguerre |
| 2004/0092806 A1 | 5/2004 | Sagon et al. |
| 2004/0116793 A1 | 6/2004 | Taimisto et al. |
| 2004/0147920 A1 | 7/2004 | Keidar |
| 2004/0162556 A1 | 8/2004 | Swanson |
| 2004/0186467 A1 | 9/2004 | Swanson et al. |
| 2004/0210136 A1 | 10/2004 | Varghese et al. |
| 2004/0215177 A1 | 10/2004 | Swanson |
| 2004/0215186 A1 | 10/2004 | Cornelius et al. |
| 2005/0033331 A1 | 2/2005 | Burnett et al. |
| 2005/0059862 A1 | 3/2005 | Phan |
| 2005/0059962 A1 | 3/2005 | Phan et al. |
| 2005/0059963 A1 | 3/2005 | Phan et al. |
| 2005/0059965 A1 | 3/2005 | Eberl et al. |
| 2005/0065506 A1 | 3/2005 | Phan |
| 2005/0065508 A1 | 3/2005 | Johnson et al. |
| 2005/0070894 A1 | 3/2005 | McClurken |
| 2005/0090817 A1 | 4/2005 | Phan |
| 2005/0119545 A1 | 6/2005 | Swanson |
| 2005/0119648 A1 | 6/2005 | Swanson |
| 2005/0119649 A1 | 6/2005 | Swanson |
| 2005/0119653 A1 | 6/2005 | Swanson |
| 2005/0119654 A1 | 6/2005 | Swanson et al. |
| 2005/0124881 A1 | 6/2005 | Kanai et al. |
| 2005/0187544 A1 | 8/2005 | Swanson et al. |
| 2005/0203597 A1 | 9/2005 | Yamazaki et al. |
| 2005/0228286 A1 | 10/2005 | Messerly et al. |
| 2005/0228504 A1 | 10/2005 | Demarais |
| 2005/0273060 A1 | 12/2005 | Levy et al. |
| 2006/0030919 A1 | 2/2006 | Mrva et al. |
| 2006/0089634 A1 | 4/2006 | Anderson et al. |
| 2006/0100522 A1 | 5/2006 | Yuan et al. |
| 2006/0161146 A1 | 7/2006 | Cornelius et al. |
| 2006/0247607 A1 | 11/2006 | Cornelius et al. |
| 2006/0247683 A1 | 11/2006 | Danek et al. |
| 2006/0253028 A1 | 11/2006 | Lam et al. |
| 2006/0253116 A1 | 11/2006 | Avitall et al. |
| 2007/0003811 A1 | 1/2007 | Zerfass et al. |
| 2007/0016054 A1 | 1/2007 | Yuan et al. |
| 2007/0016059 A1 | 1/2007 | Morimoto et al. |
| 2007/0016228 A1 | 1/2007 | Salas |
| 2007/0021744 A1 | 1/2007 | Creighton |
| 2007/0049925 A1 | 3/2007 | Phan et al. |
| 2007/0055225 A1 | 3/2007 | Dodd, III et al. |
| 2007/0073135 A1 | 3/2007 | Lee et al. |
| 2007/0088345 A1 | 4/2007 | Larson et al. |
| 2007/0165916 A1 | 7/2007 | Cloutier et al. |
| 2007/0167813 A1 | 7/2007 | Lee et al. |
| 2007/0181139 A1 | 8/2007 | Hauck |
| 2007/0238997 A1 | 10/2007 | Camus |
| 2007/0270794 A1 | 11/2007 | Anderson et al. |
| 2008/0009733 A1 | 1/2008 | Saksena |
| 2008/0015568 A1 | 1/2008 | Paul et al. |
| 2008/0025145 A1 | 1/2008 | Peszynski et al. |
| 2008/0051841 A1 | 2/2008 | Swerdlow et al. |
| 2008/0058836 A1 | 3/2008 | Moll et al. |
| 2008/0086073 A1 | 4/2008 | McDaniel |
| 2008/0091109 A1 | 4/2008 | Abraham |
| 2008/0140065 A1 | 6/2008 | Rioux et al. |
| 2008/0161705 A1 | 7/2008 | Podmore et al. |
| 2008/0161795 A1 | 7/2008 | Wang et al. |
| 2008/0161796 A1 | 7/2008 | Cao et al. |
| 2008/0195089 A1 | 8/2008 | Thiagalingam et al. |
| 2008/0228111 A1 | 9/2008 | Nita |
| 2008/0243214 A1 | 10/2008 | Koblish |
| 2008/0275428 A1 | 11/2008 | Tegg et al. |
| 2008/0281322 A1 | 11/2008 | Sherman et al. |
| 2008/0287803 A1 | 11/2008 | Li et al. |
| 2008/0300454 A1 | 12/2008 | Goto |
| 2008/0312521 A1 | 12/2008 | Solomon |
| 2008/0312713 A1 | 12/2008 | Wilfley et al. |
| 2009/0005771 A1 | 1/2009 | Lieber et al. |
| 2009/0030312 A1 | 1/2009 | Hadjicostis |
| 2009/0048591 A1 | 2/2009 | Ibrahim et al. |
| 2009/0056344 A1 | 3/2009 | Poch |
| 2009/0062790 A1 | 3/2009 | Malchano et al. |
| 2009/0062795 A1 | 3/2009 | Vakharia et al. |
| 2009/0076390 A1 | 3/2009 | Lee et al. |
| 2009/0093810 A1 | 4/2009 | Subramaniam et al. |
| 2009/0093811 A1 | 4/2009 | Koblish et al. |
| 2009/0099472 A1 | 4/2009 | Remmert et al. |
| 2009/0131932 A1 | 5/2009 | Vakharia et al. |
| 2009/0163904 A1 | 6/2009 | Miller et al. |
| 2009/0171341 A1 | 7/2009 | Pope et al. |
| 2009/0171345 A1 | 7/2009 | Miller et al. |
| 2009/0177069 A1 | 7/2009 | Razavi |
| 2009/0177111 A1 | 7/2009 | Miller et al. |
| 2009/0182316 A1 | 7/2009 | Bencini |
| 2009/0209950 A1 | 8/2009 | Starksen |
| 2009/0216125 A1 | 8/2009 | Lenker |
| 2009/0240247 A1 | 9/2009 | Rioux et al. |
| 2009/0259274 A1 | 10/2009 | Simon et al. |
| 2009/0275827 A1 | 11/2009 | Aiken et al. |
| 2009/0281541 A1 | 11/2009 | Ibrahim et al. |
| 2009/0287202 A1 | 11/2009 | Ingle et al. |
| 2009/0292209 A1 | 11/2009 | Hadjicostis |
| 2009/0299355 A1 | 12/2009 | Bencini et al. |
| 2009/0299360 A1 | 12/2009 | Ormsby |
| 2009/0306643 A1 | 12/2009 | Pappone et al. |
| 2010/0010487 A1 | 1/2010 | Phan et al. |
| 2010/0057072 A1 | 3/2010 | Roman et al. |
| 2010/0076402 A1 | 3/2010 | Mazzone et al. |
| 2010/0094274 A1 | 4/2010 | Narayan et al. |
| 2010/0106155 A1 | 4/2010 | Anderson et al. |
| 2010/0113938 A1 | 5/2010 | Park et al. |
| 2010/0145221 A1 | 6/2010 | Brunnett et al. |
| 2010/0152728 A1 | 6/2010 | Park et al. |
| 2010/0168557 A1 | 7/2010 | Deno et al. |
| 2010/0168568 A1 | 7/2010 | Sliwa |
| 2010/0168570 A1 | 7/2010 | Sliwa et al. |
| 2010/0168831 A1 | 7/2010 | Korivi et al. |
| 2010/0241117 A1 | 9/2010 | Paul et al. |
| 2010/0249599 A1 | 9/2010 | Hastings et al. |
| 2010/0249603 A1 | 9/2010 | Hastings et al. |
| 2010/0249604 A1 | 9/2010 | Hastings et al. |
| 2010/0298826 A1 | 11/2010 | Leo et al. |
| 2010/0331658 A1 | 12/2010 | Kim et al. |
| 2011/0028820 A1 | 2/2011 | Lau et al. |
| 2011/0034915 A1 | 2/2011 | Ibrahim et al. |
| 2011/0071400 A1 | 3/2011 | Hastings et al. |
| 2011/0071401 A1 | 3/2011 | Hastings et al. |
| 2011/0112569 A1 | 5/2011 | Friedman et al. |
| 2011/0125143 A1 | 5/2011 | Gross et al. |
| 2011/0130648 A1 | 6/2011 | Beeckler et al. |
| 2011/0137153 A1 | 6/2011 | Govari et al. |
| 2011/0144491 A1 | 6/2011 | Sliwa et al. |
| 2011/0144524 A1 | 6/2011 | Fish et al. |
| 2011/0160584 A1 | 6/2011 | Paul et al. |
| 2011/0237933 A1 | 9/2011 | Cohen |
| 2011/0282249 A1 | 11/2011 | Tsoref et al. |
| 2011/0319782 A1 | 12/2011 | Sweeney et al. |
| 2012/0004547 A1 | 1/2012 | Harks et al. |
| 2012/0095347 A1 | 4/2012 | Adam et al. |
| 2012/0101398 A1 | 4/2012 | Ramanathan et al. |
| 2012/0116537 A1 | 5/2012 | Liebetanz |
| 2012/0136346 A1 | 5/2012 | Condie et al. |
| 2012/0136348 A1 | 5/2012 | Condie et al. |
| 2012/0136351 A1 | 5/2012 | Weekamp et al. |
| 2012/0172698 A1 | 7/2012 | Hastings et al. |
| 2012/0172727 A1 | 7/2012 | Hastings et al. |
| 2012/0172871 A1 | 7/2012 | Hastings et al. |
| 2012/0238897 A1 | 9/2012 | Wilfley et al. |
| 2012/0310064 A1 | 12/2012 | McGee |
| 2012/0330304 A1 | 12/2012 | Vegesna et al. |
| 2013/0023784 A1 | 1/2013 | Schneider et al. |
| 2013/0023897 A1 | 1/2013 | Wallace |
| 2013/0060245 A1 | 3/2013 | Grunewald et al. |
| 2013/0066312 A1 | 3/2013 | Subramaniam et al. |
| 2013/0066315 A1 | 3/2013 | Subramaniam et al. |
| 2013/0079763 A1 | 3/2013 | Heckel et al. |
| 2013/0165926 A1 | 6/2013 | Mathur et al. |
| 2013/0172715 A1 | 7/2013 | Just et al. |
| 2013/0172742 A1 | 7/2013 | Rankin et al. |
| 2013/0172875 A1 | 7/2013 | Govari et al. |

(56) References Cited

U.S. PATENT DOCUMENTS

| | | |
|---|---|---|
| 2013/0184706 A1 | 7/2013 | Gelbart et al. |
| 2013/0190747 A1 | 7/2013 | Koblish et al. |
| 2013/0197363 A1 | 8/2013 | Rankin et al. |
| 2013/0226169 A1 | 8/2013 | Miller et al. |
| 2013/0274582 A1 | 10/2013 | Afonso et al. |
| 2013/0331739 A1 | 12/2013 | Gertner |
| 2014/0012251 A1 | 1/2014 | Himmelstein et al. |
| 2014/0058375 A1 | 2/2014 | Koblish |
| 2014/0066764 A1 | 3/2014 | Subramaniam et al. |
| 2014/0073893 A1 | 3/2014 | Bencini |
| 2014/0075753 A1 | 3/2014 | Haarer et al. |
| 2014/0081111 A1 | 3/2014 | Tun et al. |
| 2014/0081112 A1 | 3/2014 | Kim et al. |
| 2014/0081113 A1 | 3/2014 | Cohen et al. |
| 2014/0081262 A1 | 3/2014 | Koblish et al. |
| 2014/0107453 A1 | 4/2014 | Maskara et al. |
| 2014/0107636 A1 | 4/2014 | Bencini |
| 2014/0194867 A1 | 7/2014 | Fish et al. |
| 2014/0214028 A1 | 7/2014 | Gelbart et al. |
| 2014/0228713 A1 | 8/2014 | Thao et al. |
| 2014/0243917 A1 | 8/2014 | Morley et al. |
| 2014/0261985 A1 | 9/2014 | Selkee |
| 2014/0276052 A1 | 9/2014 | Rankin et al. |
| 2014/0276811 A1 | 9/2014 | Koblish et al. |
| 2014/0364843 A1 | 12/2014 | Paul et al. |
| 2014/0364848 A1 | 12/2014 | Heimbecher et al. |
| 2015/0133914 A1 | 5/2015 | Koblish |
| 2015/0133920 A1 | 5/2015 | Rankin et al. |
| 2015/0265341 A1 | 9/2015 | Koblish |
| 2015/0265348 A1 | 9/2015 | Avitall et al. |
| 2015/0342672 A1 | 12/2015 | Bencini et al. |
| 2015/0374436 A1 | 12/2015 | Subramaniam et al. |
| 2016/0100884 A1 | 4/2016 | Fay et al. |

FOREIGN PATENT DOCUMENTS

| | | |
|---|---|---|
| CA | 2848053 A1 | 3/2013 |
| CN | 1269703 A | 10/2000 |
| CN | 1455655 A | 11/2003 |
| CN | 1942145 A | 4/2007 |
| CN | 102271607 A | 12/2011 |
| CN | 102573986 A | 7/2012 |
| CN | 103917185 A | 7/2014 |
| CN | 103987336 A | 8/2014 |
| CN | 104619259 A | 5/2015 |
| CN | 104640513 A | 5/2015 |
| CN | 104661609 A | 5/2015 |
| EP | 1343426 B1 | 9/2003 |
| EP | 1343427 B1 | 9/2003 |
| EP | 1502542 A1 | 2/2005 |
| EP | 1547537 A1 | 6/2005 |
| EP | 0985423 B1 | 4/2006 |
| EP | 1717601 A2 | 11/2006 |
| EP | 1935332 A2 | 6/2008 |
| EP | 2755587 A | 7/2014 |
| EP | 2755588 A | 7/2014 |
| EP | 2136702 B1 | 7/2015 |
| JP | 2000000242 A | 1/2000 |
| JP | 200083918 A | 3/2000 |
| JP | 2000504242 A | 4/2000 |
| JP | 2002528039 A | 8/2002 |
| JP | 2003504090 A | 2/2003 |
| JP | 2004503335 A | 2/2004 |
| JP | 2006239414 A | 9/2006 |
| JP | 2007163559 A | 6/2007 |
| JP | 2007244857 A | 9/2007 |
| JP | 2009142653 A | 12/2008 |
| JP | 2009518150 A | 5/2009 |
| JP | 2010522623 A | 7/2010 |
| JP | 2011142995 A | 7/2011 |
| JP | 2011525842 A | 9/2011 |
| JP | 2012531967 A | 12/2012 |
| JP | 5336465 B2 | 11/2013 |
| JP | 2014012174 A | 1/2014 |
| JP | 2014531244 A | 11/2014 |
| JP | 2015501162 A | 1/2015 |
| JP | 2015509027 A | 3/2015 |
| KR | 20100021401 A | 2/2010 |
| KR | 101490374 B1 | 2/2015 |
| WO | WO9221278 A1 | 12/1992 |
| WO | WO9413358 A1 | 6/1994 |
| WO | WO9725916 A1 | 7/1997 |
| WO | WO9725917 A1 | 7/1997 |
| WO | WO9736541 A1 | 10/1997 |
| WO | 1997045156 A2 | 12/1997 |
| WO | WO9858681 A2 | 12/1998 |
| WO | 9909879 A1 | 3/1999 |
| WO | WO9927862 A1 | 6/1999 |
| WO | WO0029062 A2 | 5/2000 |
| WO | WO0158372 A1 | 8/2001 |
| WO | WO0164145 A1 | 9/2001 |
| WO | WO0168173 A2 | 9/2001 |
| WO | WO0205868 A2 | 1/2002 |
| WO | WO0209599 A2 | 2/2002 |
| WO | WO0219934 A1 | 3/2002 |
| WO | WO0247569 A1 | 6/2002 |
| WO | WO02102234 A2 | 12/2002 |
| WO | WO03039338 A2 | 5/2003 |
| WO | WO2007079278 A1 | 7/2007 |
| WO | WO2008046031 A2 | 4/2008 |
| WO | WO2008118992 A1 | 10/2008 |
| WO | WO2009032421 A2 | 3/2009 |
| WO | 2009048824 A1 | 4/2009 |
| WO | 2009048943 A | 4/2009 |
| WO | 2010054409 A1 | 5/2010 |
| WO | WO2010056771 A1 | 5/2010 |
| WO | 2010082146 A1 | 7/2010 |
| WO | 2011008444 A1 | 1/2011 |
| WO | 2011033421 A1 | 3/2011 |
| WO | WO2011024133 A1 | 3/2011 |
| WO | WO2011089537 A1 | 7/2011 |
| WO | 2011101778 A1 | 8/2011 |
| WO | WO2011095937 A1 | 8/2011 |
| WO | 2012001595 A1 | 1/2012 |
| WO | WO2012001595 A1 | 1/2012 |
| WO | WO2012049621 A1 | 4/2012 |
| WO | WO2012066430 A1 | 5/2012 |
| WO | 2012161880 A1 | 11/2012 |
| WO | WO2012151301 A1 | 11/2012 |
| WO | 2012166239 A1 | 12/2012 |
| WO | 2013040201 A2 | 3/2013 |
| WO | 2013040297 A1 | 3/2013 |
| WO | 2014072879 A2 | 5/2014 |
| WO | 2014152575 A2 | 9/2014 |
| WO | 2015143061 A1 | 9/2015 |
| WO | 2015183635 A1 | 12/2015 |

OTHER PUBLICATIONS

Hayerkamp, W., et. al. Coagulation of Ventricular Myocardium Using Radiofrequency Alternating Current: Bio-Physical Aspects and Experimental Findings. PACE, 12:187-195, Jan. 1989, Part II.
International Preliminary Examination Report issued in PCT/US2013/060183, completed Mar. 24, 2015, 6 pages.
International Preliminary Report on Patentability issued in PCT/US2013/056211, completed Feb. 24, 2015, 5 pages.
International Preliminary Report on Patentability issued in PCT/US2013/060194, mailed Mar. 24, 2015, 6 pages.
International Search Report and Written Opinion issued in PCT/US2008/058324, dated Aug. 18, 2008, 11 pages.
International Search Report and Written Opinion issued in PCT/US2012/055309, mailed Nov. 19, 2012, 13 pages.
International Search Report and Written Opinion issued in PCT/US2013/056211, mailed Jan. 20, 2014.
International Search Report and Written Opinion issued in PCT/US2013/060183, mailed Jan. 27, 2014, 10 pages.
International Search Report and Written Opinion issued in PCT/US2013/060194, mailed Jan. 29, 2014.
International Search Report and Written Opinion issued in PCT/US2013/060194, mailed Jan. 29, 2014, 10 pages.
International Search Report and Written Opinion issued in PCT/US2015/021300, mailed Jun. 9, 2015, 11 pages.

(56) References Cited

OTHER PUBLICATIONS

International Search Report and Written Opinion issued in PCT/US2015/031591, mailed Aug. 17, 2015, 11 pages.
Machi MD, Junji, "Prevention of Dispersive Pad Skin Burns During RFA by a Simple Method", Editorial Comment, Surg Laparosc Endosc Percutan Tech, vol. 13, No. 6, Dec. 2003, pp. 372-373.
Neufeld, Gordon R. et al., "Electrical Impedance Properties of the Body and the Problem of Alternate-site Burns During Electrosurgery", Medical Instrumentation, vol. 19, No. 2, Mar.-Apr. 1985, pp. 83-87.
Partial International Search Report issued in PCT/US2012/055155, mailed Dec. 20, 2012, 7 pages.
Pires, L. A., et. al. Temperature-guided Radiofrequency Catheter Ablation of Closed-Chest Ventricular Myocardium with a Novel Thermistor-Tipped Catheter. American Heart Journal, 127(6):1614-1618, Jun. 1994.
Ring, E. R., et. al. Catheter Ablation of the Ventricular Septum with Radiofrequency Energy. American Heart Journal, 117(6):1233-1240, Jun. 1989.
Steinke, Karin et al., "Dispersive Pad Site burns With Modern Radiofrequency Ablation Equipment", Surg Laparosc Endosc Percutan Tech, vol. 13, No. 6, Dec. 2003, pp. 366-371.
Extended European Search Report issued in EP Application No. 15174537.9, issued Mar. 2, 2016, 7 pages.
International Preliminary Examination Report issued in PCT/US2013/060612, completed Mar. 24, 2015, 10 pages.
International Preliminary Report on Patentability issued in PCT/US2008/058324, mailed Sep. 29, 2009, 9 pages.
International Preliminary Report on Patentability issued in PCT/US2012/055155, issued Mar. 18, 2014, 11 pages.
International Preliminary Report on Patentability issued in PCT/US2012/055309, issued on Mar. 18, 2014, 8 pages.
International Preliminary Report on Patentability issued in PCT/US2013/058105, completed Mar. 10, 2015.
International Preliminary Report on Patentability issued in PCT/US2014/027491, mailed Sep. 24, 2015, 12 pages.
International Search Report and Written Opinion issued in PCT/US2012/031819, mailed Sep. 27, 2012, 16 pages.
International Search Report and Written Opinion issued in PCT/US2012/055155, mailed Mar. 11, 2013, 19 pages.
International Search Report and Written Opinion issued in PCT/US2012/072061, mailed Mar. 21, 2013, 9 pages.
International Search Report and Written Opinion issued in PCT/US2013/020503, mailed Mar. 20, 2013, 10 pages.
International Search Report and Written Opinion issued in PCT/US2013/058105, mailed Nov. 22, 2013, 16 pages.
International Search Report and Written Opinion issued in PCT/US2013/060612, mailed Feb. 28, 2014, 16 pages.
International Search Report and Written Opinion issued in PCT/US2014/027491, mailed Sep. 23, 2014, 17 pages.
International Search Report and Written Opinion issued in PCT/US2015/055173, mailed Jan. 18, 2016, 11 pages.
International Search Report and Written Opinion issued in PCT/US2015/057242, mailed Jan. 15, 2016, 11 pages.
Invitation to Pay Additional Fees and Partial International Search Report issued in PCT/US2014/027491, mailed Jul. 28, 2014, 5 pages.
Patriciu, A. et al., "Detecting Skin Burns Induced by Surface Electrodes", published in Engineering in Medicine and Biology Society, 2001. Proceedings of the 23rd Annual International Conference of the IEEE, vol. 3, pp. 3129-3131.
International Search Report and Written Opinion issued in PCT/US2013/021013, mailed Apr. 5, 2013, 14 pages.
Piorkowski, Christopher et al., "First in Human Validation of Impedance-Based Catheter Tip-to-Tissue Contact Assessment in the Left Atrium", Journal of Cardiovascular Electrophysiology, vol. 20, No. 12, Dec. 1, 2009, pp. 1366-1373.
Price, Adam et al., "Novel Ablation Catheter Technology that Improves Mapping Resolution and Monitoring of Lesion Maturation", The Journal of Innovations in Cardiac Rhythm Management, vol. 3, 2002, pp. 599-609.
Price, Adam et al., "PO3-39 Pin Electrodes Improve Resolution: Enhanced Monitoring of Radiofrequency Lesions in the Voltage and Frequency Domains", Heart Rhythm 2010, 31st Annual Scientific Sessions, May 12-15, in Denver Colorado.
Zachary, J.M. et al., "PO4-86 Pin Electrodes Provide Enhanced Resolution Enabling Titration of Radiofrequency Duration to Lesion Maturation", Heart Rhythm 2011, 32 Annual Scientific Sessions, May 4-7, San Francisco, CA.
Extended European Search Report issued in EP Application 16182627.6, mailed Nov. 8, 2016, 5 pages.
International Preliminary Report on Patentability issued in PCT/US2015/021300 mailed Sep. 29, 2016, 7 pages.
International Search Report and Written Opinion issued in PCT/US2015/066874, mailed Apr. 1, 2016, 11 pages.
International Search Report and Written Opinion issued in PCT/US2016/028006 mailed Jul. 12, 2016, 12 pages.
International Preliminary Report on Patentability issued in PCT/US2015/031591, mailed Dec. 6, 2016, 7 pages.

ELECTROPHYSIOLOGY SYSTEM AND METHODS

CROSS-REFERENCE TO RELATED APPLICATION

This application is a continuation of U.S. application Ser. No. 13/738,562 filed Jan. 10, 2013, which claims the benefits of Provisional Application No. 61/715,032, filed Oct. 17, 2012, and Provisional Application No. 61/585,083 filed Jan. 10, 2012, each of which are incorporated herein by reference in their entirety.

TECHNICAL FIELD

The present disclosure relates to therapies for cardiac conditions. More particularly, the present disclosure relates to methods and systems for ablation of cardiac tissue for treating cardiac arrythmias.

BACKGROUND

Aberrant conductive pathways disrupt the normal path of the heart's electrical impulses. For example, conduction blocks can cause the electrical impulse to degenerate into several circular wavelets that disrupt the normal activation of the atria or ventricles. The aberrant conductive pathways create abnormal, irregular, and sometimes life-threatening heart rhythms called arrhythmias. Ablation is one way of treating arrhythmias and restoring normal contraction. The sources of the aberrant pathways (called focal arrhythmia substrates) are located or mapped using mapping electrodes situated in a desired location. After mapping, the physician may ablate the aberrant tissue. In radio frequency (RF) ablation, RF energy is directed from the ablation electrode through tissue to an electrode to ablate the tissue and form a lesion.

SUMMARY

In Example 1, the present invention is an electrophysiology method comprising advancing a distal portion of an ablation catheter intravascularly to a location proximate myocardial tissue within a chamber of a heart. The distal portion of the ablation catheter includes a tissue ablation electrode and a plurality of microelectrodes circumferentially distributed about the tissue ablation electrode and electrically isolated therefrom. The tissue ablation electrode is configured to apply ablation energy to the myocardial tissue, and the plurality of microelectrodes define a plurality of bipolar microelectrode pairs, each bipolar microelectrode pair configured to generate an output signal. The method further comprises acquiring the output signals from each of the bipolar microelectrode pairs, and comparing an amplitude of the output signal from each of the bipolar microelectrode pairs to the amplitudes of the output signals from the other of the plurality of bipolar microelectrode pairs. The method further comprises displaying to a clinician a visual indication of a proximity of the tissue ablation electrode to the myocardial tissue. The visual indication includes an indication that the tissue ablation electrode is in contact with the myocardial tissue if a difference between the amplitude of any one of the output signals and the amplitude of any one or more of the other output signals exceeds a predetermined threshold, an indication that the tissue ablation electrode is not in contact with the myocardial tissue if the difference between the amplitude of any one of the output signals and the amplitude of any one or more of the other output signals does not exceed a predetermined threshold.

In Example 2, the method of Example 1, wherein the acquiring and comparing steps are performed by a mapping processor operatively coupled to the microelectrodes.

In Example 3, the method of either of Examples 1 or 2, wherein the plurality of microelectrodes include three microelectrodes defining first, second and third bipolar microelectrode pairs.

In Example 4, the method of Example 3, wherein the three microelectrodes are disposed at the same longitudinal position along the tissue ablation electrode.

In Example 5, the method of any of Examples 1-4, further comprising displaying to the clinician a visual indication of an orientation of the tissue ablation electrode relative to the myocardial tissue based on the amplitudes of the output signals from the first, second and third bipolar microelectrode pairs.

In Example 6, of any of Examples 1-5, further comprising acquiring output signals from one or more ring electrodes located on the ablation catheter proximal to the tissue ablation electrode, comparing the output signal from each bipolar microelectrode pair with the ring electrode output signals to identify intrinsic cardiac activation signals in the bipolar microelectrode pair signals, and generating an output to a display indicating a gap in an ablation lesion set at the location of any bipolar microelectrode pairs that sensed the intrinsic cardiac activation signals.

In Example 7, the method of any of Examples 1-6, wherein the ablation catheter further comprises a plurality of irrigation ports in the tissue ablation electrode fluidly and operatively coupled to an irrigation fluid reservoir and pump.

In Example 8, the method of any of Examples 1-7, wherein the ablation catheter further includes a proximal handle having a control element for manipulation by a user, and wherein advancing the distal portion of the ablation catheter includes manipulating the control element to deflect the distal portion for positioning the tissue ablation electrode adjacent to the myocardial tissue.

In Example 9, an electrophysiology system comprising an ablation catheter, a radiofrequency (RF) generator, and a mapping processor. The ablation catheter includes a flexible catheter body having a distal portion, a tissue ablation electrode, and a plurality of microelectrodes. The tissue ablation electrode is configured to apply ablation energy to the myocardial tissue. The plurality of microelectrodes are circumferentially distributed about the tissue ablation electrode and electrically isolated therefrom, and define a plurality of bipolar microelectrode pairs, each bipolar microelectrode pair configured to generate an output signal. The RF generator is operatively coupled to the tissue ablation electrode for generating the ablation energy to be conveyed to the tissue ablation electrode. The mapping processor is configured to acquire the output signals from each of the bipolar microelectrode pairs, compare an amplitude of the output signal from each of the bipolar microelectrode pairs to the amplitudes of the output signals from the other of the plurality of bipolar microelectrode pairs, and generate an output to a display to provide a clinician with a visual indication of a proximity of the tissue ablation electrode to the myocardial tissue. The visual indication includes an indication that the tissue ablation electrode is in contact with the myocardial tissue if a difference between the amplitude of any one of the output signals and the amplitude of any one or more of the other output signals exceeds a predetermined threshold, and an indication that the tissue ablation electrode is not in contact with the myocardial tissue if the difference between the amplitude of any one of the output signals and the amplitude of any one or more of the other output signals does not exceed a predetermined threshold.

In Example 10, the system of Example 9, wherein the plurality of microelectrodes include three microelectrodes defining first, second and third bipolar microelectrode pairs.

In Example 11, the system of claim either of Examples 9 or 10, wherein the three microelectrodes are disposed at the same longitudinal position along the tissue ablation electrode.

In Example 12, the system of any of Examples 9-11, wherein the mapping processor is further configured to generate an output to a display to provide the clinician with a visual indication of an orientation of the tissue ablation electrode relative to the myocardial tissue based on the amplitudes of the output signals from the first, second and third bipolar microelectrode pairs.

In Example 13, the system of any of Examples 9-12, wherein the mapping processor is further configured to acquire output signals from one or more ring electrodes located on the ablation catheter proximal to the tissue ablation electrode, compare the output signals from the bipolar microelectrode pairs with the ring electrode output signals to identify sensed intrinsic cardiac activation signals in the bipolar microelectrode pair output signals, and generate an output to the display indicating a gap in an ablation lesion pattern at the location of the bipolar microelectrode pairs that sensed the intrinsic cardiac activation signals.

In Example 14, the system of any of Examples 9-13, wherein the ablation catheter further comprises a plurality of irrigation ports in the tissue ablation electrode fluidly and operatively coupled to an irrigation fluid reservoir and pump.

In Example 15, the system of any of Examples 9-14, wherein the ablation catheter further includes a proximal handle having a control element for manipulation by a user, and wherein the distal portion of the ablation catheter is deflectable upon manipulation of the control element.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
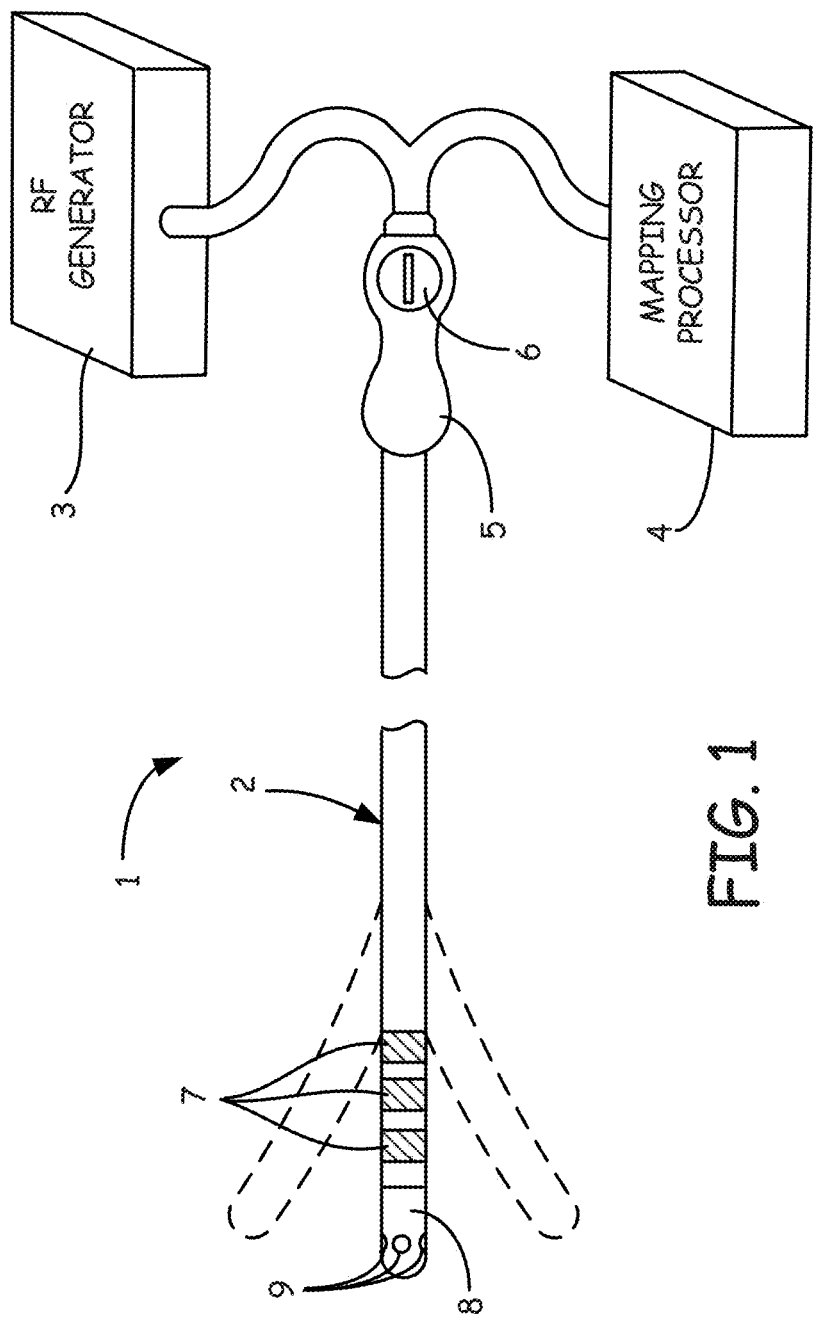
FIG. 1 is a schematic illustration of a radio frequency (RF) ablation system 1 according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration of a radio frequency (RF) ablation system 1 according to one embodiment of the present invention. As shown in FIG. 1, the system 1 includes an ablation catheter 2, an RF generator 3, and a mapping processor 4. The ablation catheter 2 is operatively coupled to both the RF generator 2 and the mapping processor 4, as will be described in greater detail herein. As further shown, the ablation catheter 2 includes a proximal handle 5 having a control knob 6, a flexible body having a distal portion including a plurality of ring electrodes 7, a tissue ablation electrode 8, and a plurality of mapping microelectrodes 9 (also referred to herein as "pin" electrodes) disposed within and electrically isolated from the tissue ablation electrode 8.

In various embodiments, the ablation catheter 2 is configured to be introduced through the vasculature of the patient, and into one of the chambers of the heart, where it can be used to map and ablate myocardial tissue using the microelectrodes 9 and the tissue ablation 8. Thus, the tissue ablation electrode 8 is configured to apply ablation energy to the myocardial tissue. In the illustrated embodiment, the ablation catheter 2 is steerable, such that the distal portion can be deflected (as indicated by the dashed outlines in FIG. 1) by manipulation of the control knob 6. In other embodiments, the distal portion of the ablation catheter 2 has a pre-formed shape adapted to facilitate positioning the tissue ablation electrode 8 and the microelectrodes 9 adjacent to specific target tissue. In one such embodiment, the pre-formed shape is generally circular or semi-circular and is oriented in a plane transverse to the general direction of the catheter body.

In various embodiments, the microelectrodes 9 are circumferentially distributed about the tissue ablation electrode 8 and electrically isolated therefrom. The microelectrodes 9 can be configured to operate in unipolar or bipolar sensing modes. In various embodiments, the plurality of microelectrodes 9 define a plurality of bipolar microelectrode pairs, each bipolar microelectrode pair being configured to generate an output signal corresponding to a sensed electrical activity of the myocardial tissue proximate thereto. The generated output signals from the microelectrodes 9 can be sent to the mapping processor 4 for processing as described herein.

Figure 3:
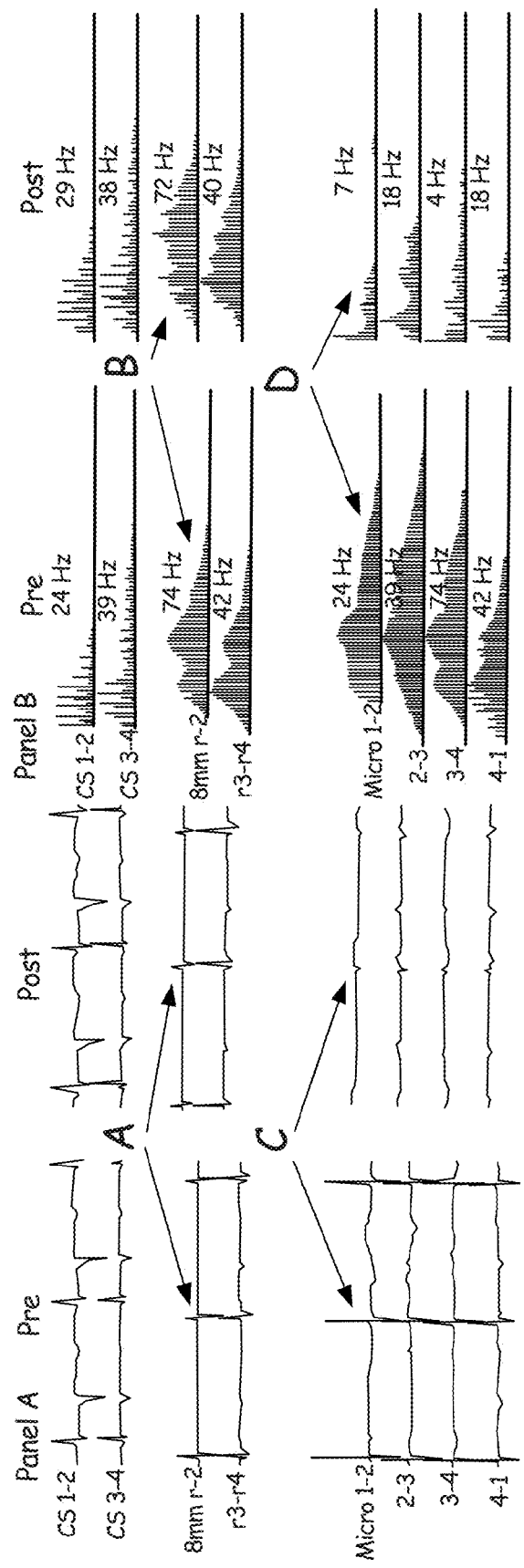
FIG. 3 illustrates a comparison between changes in voltage (panel A) and frequency spectra (panel B) pre- and post-ablation for each of the catheters illustrated in FIG. 2.
Figure 4:
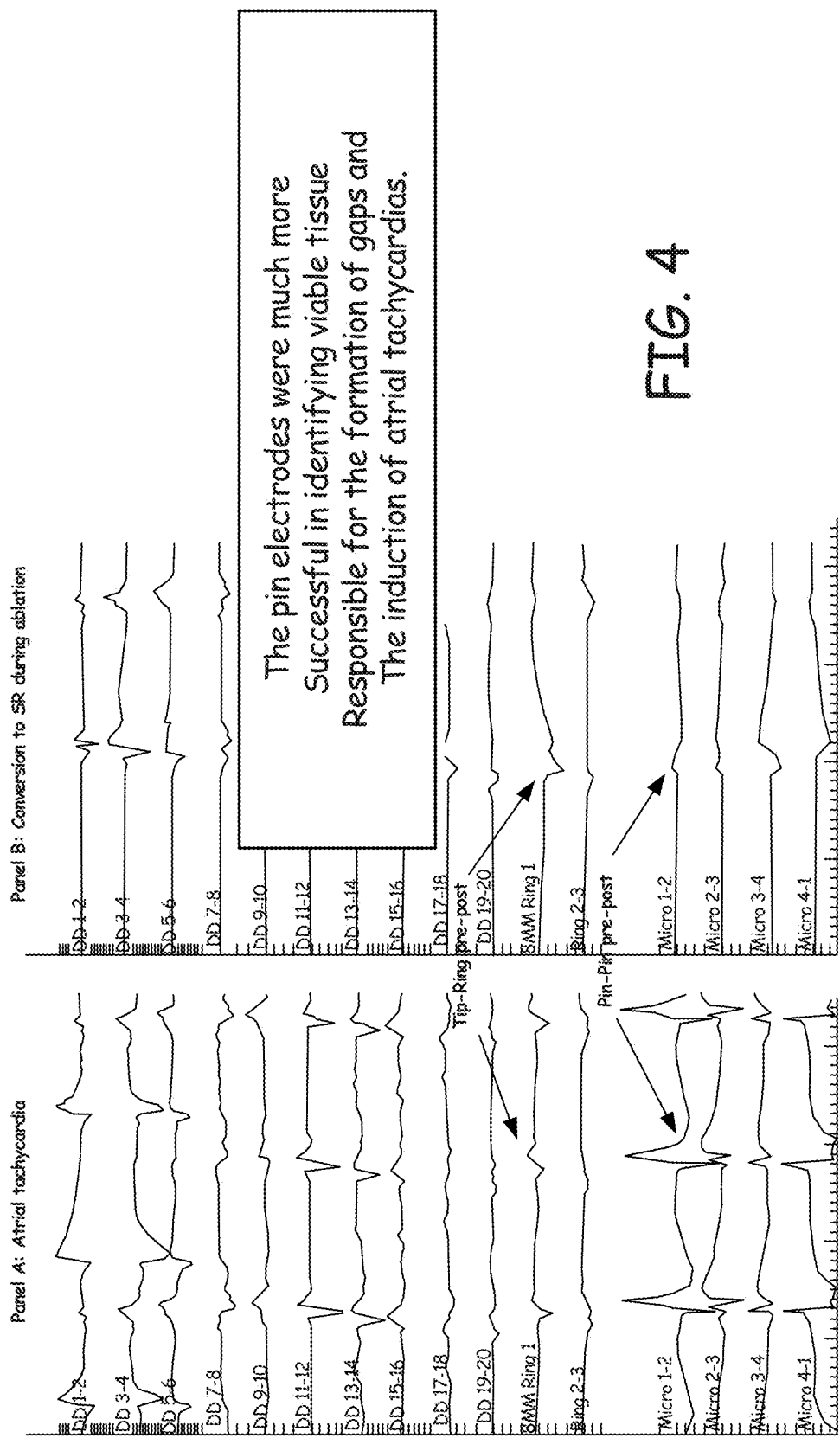
FIG. 4 illustrates a comparison of measured signal amplitude pre- and post-ablation during atrial tachycardia.

Exemplary catheters that can be used as the ablation catheter 2 can include those described in U.S. Patent App. Pub. Nos. US2008l0243214 entitled "High Resolution Electrophysiology Catheter," and 2010/0331658, entitled "Map and Ablate Open Irrigated Hybrid Catheter," which are hereby incorporated by reference in their entireties for all purposes. In various exemplary embodiments, the tissue ablation electrode 8 can have a length of between 6 and 14 mm, and a plurality of microelectrodes 9 equally spaced about the circumference of the tissue ablation electrode. In one embodiment, the tissue ablation electrode 8 can have an axial length of about 8 mm. In one embodiment, the ablation catheter 2 includes at least three microelectrodes 9 equally spaced about the circumference of the tissue ablation electrode 8 and at the same longitudinal position along the longitudinal axis of the tissue ablation electrode 8, the microelectrodes 9 forming at least first, second and third bipolar microelectrode pairs. In one embodiment, the catheter 2 includes a forward-facing microelectrode 9 generally centrally-located within the tissue ablation electrode 8. An exemplary such RF ablation catheter is illustrated in FIGS. 3 and 4 of the aforementioned U.S. Patent Application Pub. No. 2008/0243214.

In some embodiments, microelectrodes 9 can be located at other positions along the ablation catheter 2 in addition to or in lieu of the microelectrodes 9 in the tissue ablation electrode 8.

In various embodiments, the tissue ablation electrode 8 has an exterior wall that defines an open interior region (not shown). The exterior wall includes mapping electrode openings for accommodating the microelectrodes 9, and, in some embodiments, irrigation ports (not shown). The irrigation ports, when present, are in fluid communication an external irrigation fluid reservoir and pump (not shown) for supplying irrigation fluid to the myocardial tissue being mapped and/or ablated. Exemplary irrigated catheters for use as the catheter 2 can be any of the catheters described in the aforementioned U.S. Patent App. Pub. No. 2010/0331658. In various embodiments, the catheter system may also include noise artifact isolators (not shown), wherein the microelectrodes 9 are electrically insulated from the exterior wall by the noise artifact isolators.

In various embodiments, the mapping processor 4 is configured to detect, process, and record electrical signals within the heart via the ablation catheter 2. Based on these electrical signals, a physician can identify the specific target tissue sites within the heart, and ensure that the arrhythmia causing substrates have been electrically isolated by the ablative treatment. The mapping processor 4 is configured to process the output signals from the microelectrodes 9 and/or the ring electrodes 7, and to generate an output to a display (not shown) for use by the physician. In some embodiments, the display can include electrocardiograms (ECG) information, which can be analyzed by the user to determine the existence and/or location of arrhythmia substrates within the heart and/or determine the location of the ablation catheter 2 within the heart. In various embodiments, the output from the mapping processor 4 can be used to provide, via the display, an indication to the clinician about a characteristic of the ablation catheter 2 and/or the myocardial tissue being mapped.

The RF generator 3 is configured to deliver ablation energy to the ablation catheter 2 in a controlled manner in order to ablate the target tissue sites identified by the mapping processor 4. Ablation of tissue within the heart is well known in the art, and thus for purposes of brevity, the RF generator 3 will not be described in further detail. Further details regarding RF generators are provided in U.S. Pat. No. 5,383,874, which is expressly incorporated herein by reference. Although the mapping processor 4 and RF generator 3 are shown as discrete components, they can alternatively be incorporated into a single integrated device.

The RF ablation catheter 2 as described may be used to perform various diagnostic functions to assist the physician in an ablation treatment. For example, in some embodiments, the catheter is used to ablate cardiac arrhythmias, and at the same time provide real-time assessment of a lesion formed during RF ablation. Real-time assessment of the lesion may involve any of monitoring surface and/or tissue temperature at or around the lesion, reduction in the electrocardiogram signal, a drop in impedance, direct and/or surface visualization of the lesion site, and imaging of the tissue site (e.g., using computed tomography, magnetic resonance imaging, ultrasound, etc.). In addition, the presence of the microelectrodes within the RF tip electrode can operate to assist the physician in locating and positioning the tip electrode at the desired treatment site, and to determine the position and orientation of the tip electrode relative to the tissue to be ablated.

Figure 2:
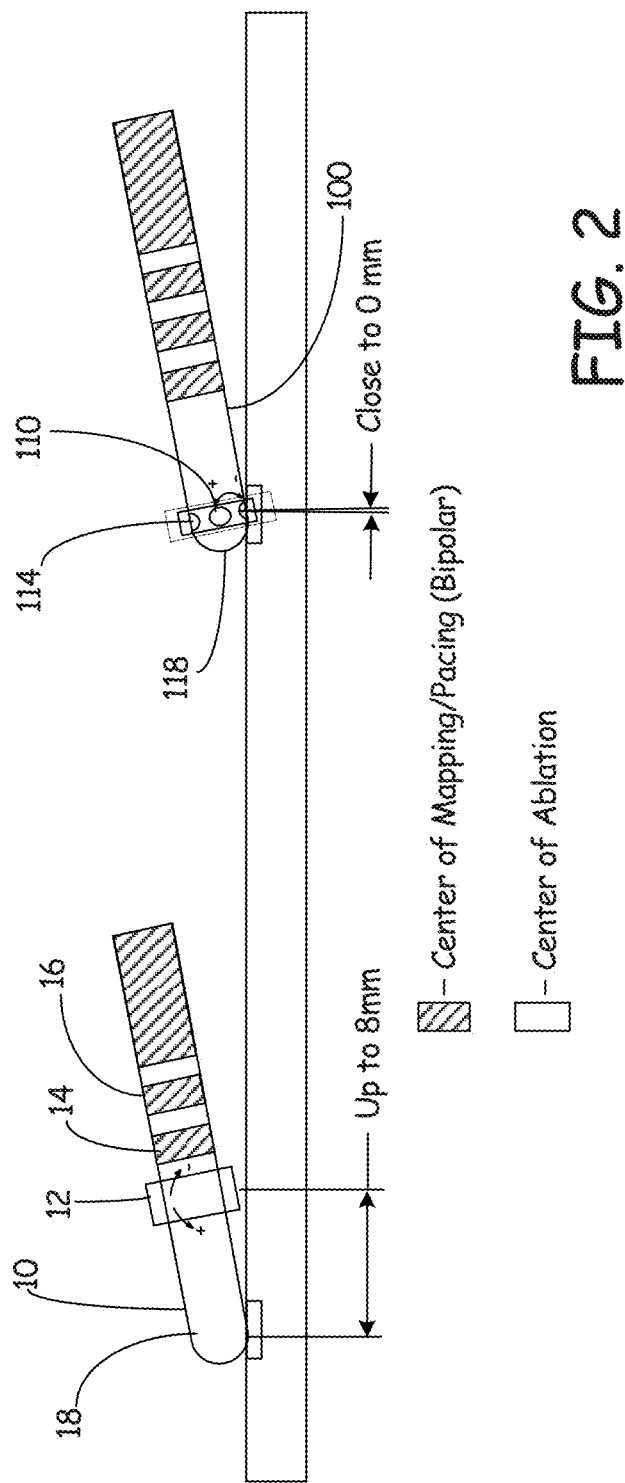
FIG. 2 is a schematic illustration showing a conventional ablation catheter on the left and an embodiment of a high-resolution ablation catheter of the present disclosure on the right.

FIG. 2 is a schematic illustration showing a conventional ablation catheter 10 (i.e., an ablation catheter lacking any microelectrodes within the tissue ablationelectrode) on the left and an embodiment of a high-resolution ablation catheter 100 of the present disclosure on the right. For cardiac mapping, the conventional catheter relies on conventional ring electrodes 12, 14, 16 disposed along the mapping electrodes a distance from the ablation tip electrode 18, resulting in a large distance between the center of mapping/pacing and the center of ablation. The catheter of the present disclosure, in contrast, includes the mapping microelectrodes 110 in mapping electrode openings 114 in the ablation tip electrode 118 to allow the center of mapping/pacing to be in substantially the same location as the center of ablation.

FIG. 3 illustrates a comparison between changes in voltage (panel A) and frequency spectra (panel B) pre- and post-ablation for each of the catheters illustrated in FIG. 2. As is shown, the tip-to-ring signal changes in the conventional ablation catheter were minimal for both the voltage and frequency domains (arrows A and B). In contrast, the recorded changes from pin to pin (i.e., between mapping micro electrodes) in the catheter of the present disclosure were profound (arrows C and D).

FIG. 4 illustrates a comparison of measured signal amplitude pre- and post-ablation during atrial tachycardia. As shown, the tip-to-ring again signal changes in the conventional ablation catheter (top arrows) were small compared to the pin-to-pin signal changes. Thus, the pin electrodes were much more successful in identifying viable tissue responsible for the formation of gaps and the induction of atrial tachycardias.

Figure 5:
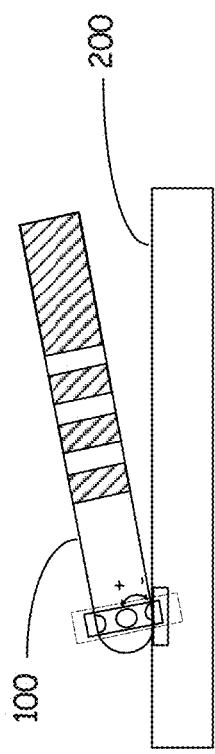
FIG. 5 is a schematic illustration showing the catheter of FIG. 2 oriented generally parallel to the surface of the cardiac tissue to be mapped and ablated.
Figure 6A:
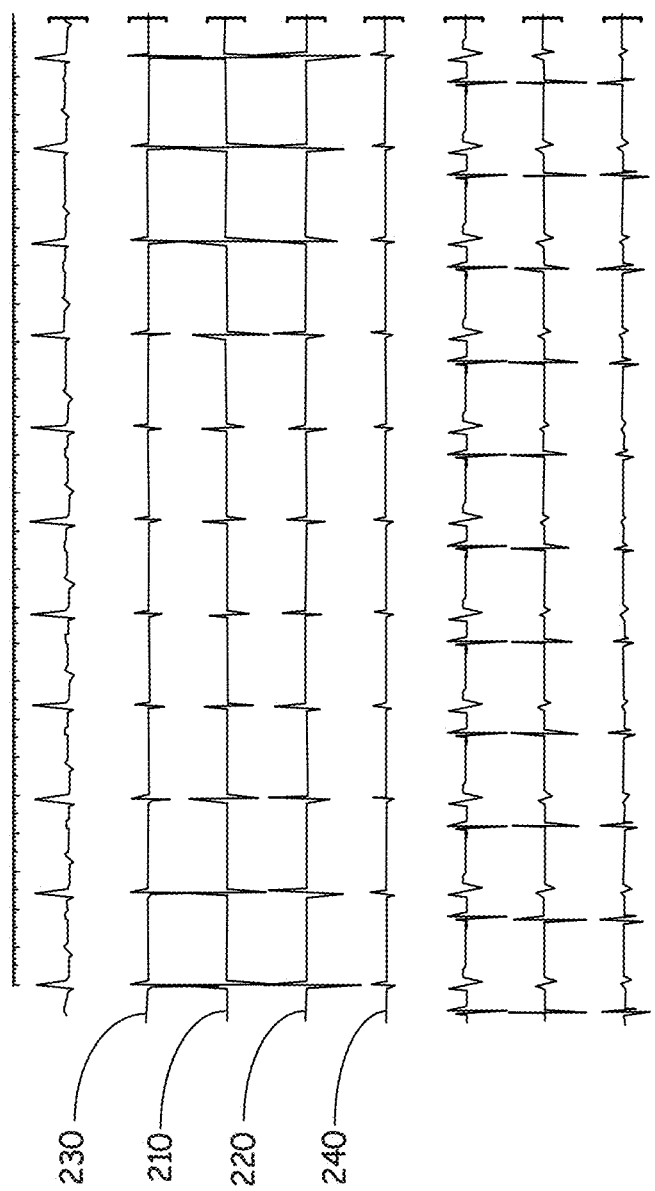
FIGS. 6A and 6B illustrate the amplitudes of the cardiac electrical signals sensed by the microelectrodes and also the ring electrodes on the catheter of FIG. 2.
Figure 6B:
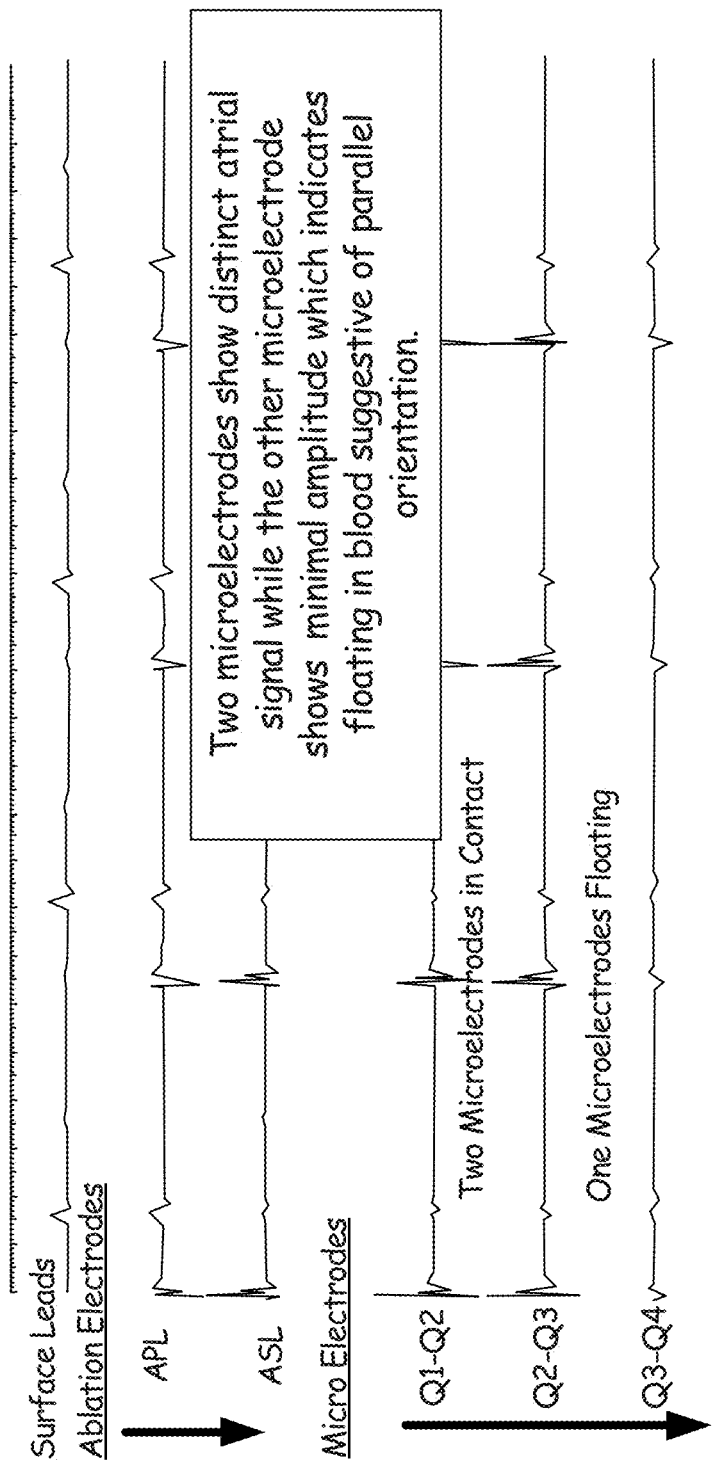

As explained previously, the microelectrodes 110 can advantageously provide feedback on electrode contact and tip electrode orientation within the heart. FIG. 5 is a schematic illustration showing the catheter 100 oriented generally parallel to the surface 200 of the cardiac tissue to be mapped and ablated. FIGS. 6A and 6B illustrate the amplitudes of the cardiac electrical signals sensed by the microelectrodes 110 and also the ring electrodes on the catheter 100, which data can be used to implement a method for determining electrode contact and the orientation of the catheter tip. In FIGS. 6A and 6B, the ECG traces of bipolar pairs of microelectrodes 110 are illustrated, as indicated by the labels defined and their corresponding ECG signals are illustrated. Specifically, in FIG. 6A, an ablation catheter having four microelectrodes (labeled 49, 50, 51 and 52) distributed about the circumference of the tissue ablation electrode, such that the labels 49-50, 50-51, 51-52 and 49-52 designate respective bipolar microelectrode pairs of adjacent microelectrodes. Similarly, in the example shown in FIG. 6B, the ECG traces for three bipolar microelectrode pairs (labeled Q1-Q2, Q2-Q3, and Q3-Q4) are illustrated.

In the illustrated example, as shown in FIG. 6A, two bipolar microelectrode pairs (indicated by references 210, 220) each show a distinct atrial signal while the other bipolar microelectrode pairs (indicated by references 230, 240) show minimal amplitude. The mapping microelectrode(s) with a signal of minimal amplitude indicates floating in blood, which is suggestive of a parallel tip orientation. FIG. 6B illustrates a similar result, with two of the bipolar microelectrode microelectrode pairs (the pairs Q1-Q2 and Q2-Q3) showing an atrial signal and one pair (Q3-Q4) showing a minimal signal amplitude. This data allows the system 1 to confirm both tip contact with the cardiac tissue as well as orientation of the tip relative to the tissue surface, which could not be accomplished using only the ring electrodes on the catheter 100, all of which show minimal signal amplitude (as shown in FIGS. 6A and 6B) suggesting no tissue contact.

Figure 7:
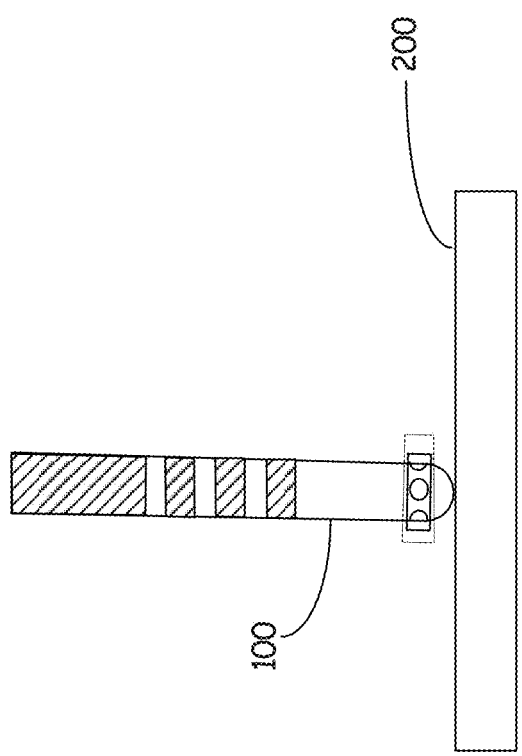
FIG. 7 is a schematic illustration showing the catheter of FIG. 2 oriented generally perpendicular to the surface of the cardiac tissue to be mapped and ablated.
Figure 8:
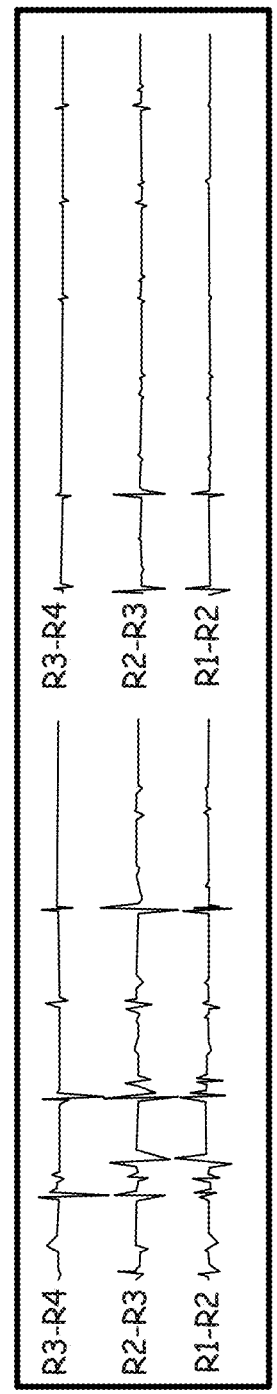
FIG. 8 illustrates the corresponding electrogram signals for the configuration of FIG. 7.

FIG. 7 is a schematic illustration showing the catheter 100 oriented generally perpendicular to the surface 200 of the cardiac tissue to be mapped and ablated, and FIG. 8 illustrates the corresponding electrogram signals for the configuration of FIG. 7. As can be seen in FIG. 8, all bipolar microelectrode pairs (designated by R3-R1, R2-R3 and R1-R2) show substantially equal signal amplitude, indicating that all of the microelectrodes are floating in blood and not in contact with the surface 200.

Figure 9:
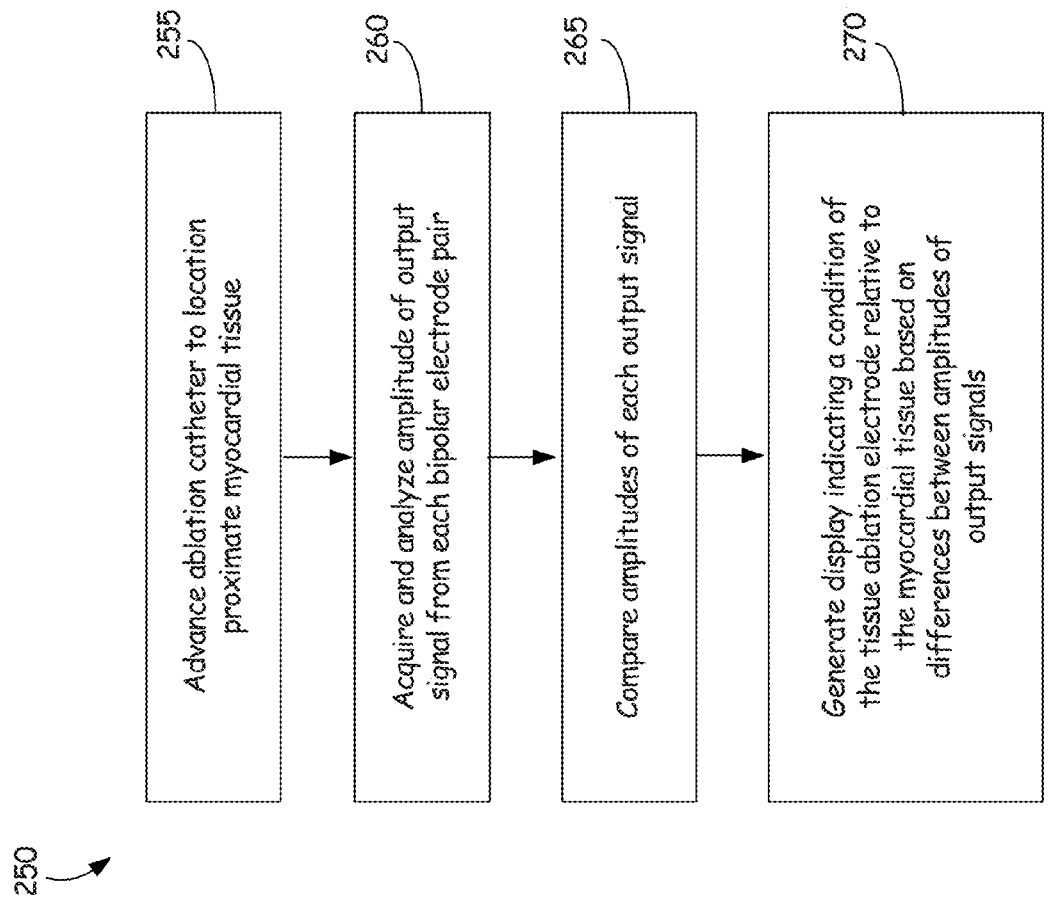
FIG. 9 is a flow chart illustrating a method for assessing a characteristic (e.g., tissue contact) of the tissue ablation electrode of the ablation catheter of FIG. 1 or 2 according to the various embodiments.

FIG. 9 is a flow chart illustrating a method 250 for assessing a characteristic (e.g., tissue contact) of the tissue ablation electrode of the ablation catheter 2, 100 according to the various embodiments as described herein. As shown in FIG. 9, the method 250 includes, at step 255, first advancing the distal portion of the ablation catheter intravascularly to a location proximate the myocardial tissue to be mapped and/or ablated. The ablation catheter may be the ablation catheter 2 or 100 described herein. In the various embodiments, the particular ablation catheter includes a plurality of microelectrodes in the tissue ablation electrode defining a plurality of bipolar pairs of microelectrodes. In one embodiment, the ablation catheter includes at least three microelectrodes disposed about the circumference of the tissue ablation electrode defining first, second and third bipolar microelectrode pairs.

Next, at step 260, the system acquires the output signal from each bipolar electrode pair. Subsequently, as shown at step 265, the method compares the amplitude of the output signal from each of the bipolar microelectrode pairs to the amplitudes of the output signals from the other of the plurality of bipolar microelectrode pairs. Then, as indicated at step 70, a display is generated indicating a condition of the tissue ablation electrode relative to the myocardial tissue based on differences between amplitudes of output signals.

In one embodiment, the displayed condition can include a visual indication of the proximity of the tissue ablation electrode to the myocardial tissue. In one embodiment, this visual indication of proximity can include an indication that the tissue ablation electrode is in contact with the myocardial tissue if the difference between the amplitude of any one of the output signals and the amplitude of any one or more of the other output signals exceeds a predetermined threshold. In addition, the visual indication of proximity can include an indication that the tissue ablation electrode is not in contact with the myocardial tissue if the difference between the amplitude of any one of the output signals and the amplitude of any one or more of the other output signals does not exceed a predetermined threshold.

In various embodiments, the steps of acquiring and comparing the output signals from the bipolar microelectrode pairs are performed by the mapping processor, which is operatively coupled to the microelectrodes (see FIG. 1).

In one embodiment, the microelectrodes, and consequently, the first, second and third bipolar microelectrode pairs, each have a known position with respect to the tissue ablation electrode and the other microelectrodes. In such embodiments, the method 250 can further include displaying to the clinician a visual indication of the orientation of the tissue ablation electrode relative to the myocardial tissue based on the amplitudes of the output signals from the first, second and third bipolar microelectrode pairs.

In one embodiment, the method 250 can be carried out using an irrigated ablation catheter having a plurality of irrigation ports in the tissue ablation electrode fluidly and operatively coupled to an irrigation fluid reservoir and pump, and the method 250 includes supplying an irrigation fluid through the irrigation ports during the mapping and/or ablation procedures.

Figure 10:
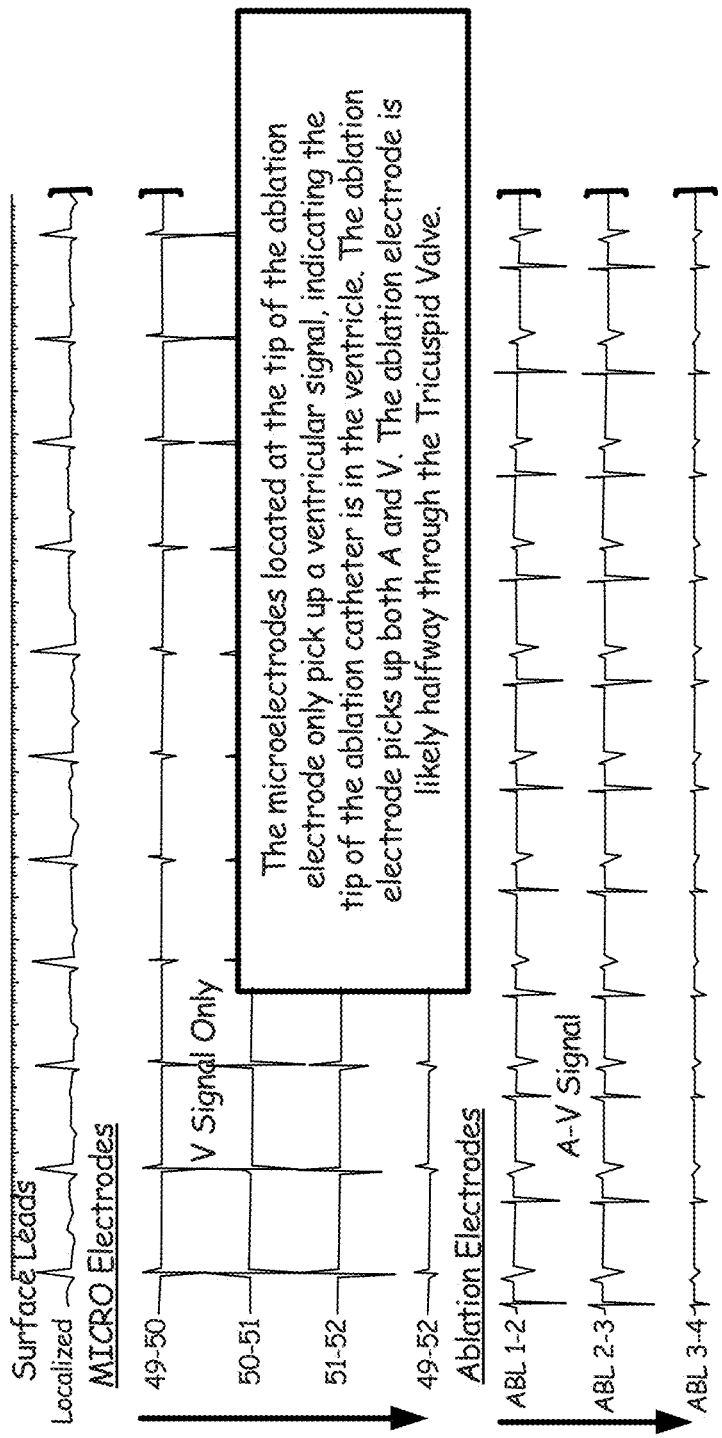
FIG. 10 illustrates an output from a plurality of bipolar microelectrode pairs that can be used by the system of FIG. 1 in a method for determining the tip location when far field noise is suspected.

Still other methods may advantageously be facilitated by the presence and configurations of the microelectrodes of the ablation catheters 2, 100 described herein. For example, FIG. 10 illustrates an ECG generated from an output from a plurality of bipolar microelectrode pairs (labeled 49-50, 50-51, 51-52 and 49-52, respectively) that can be used by the system 1 in a method for determining the tip location when far field noise is suspected. In the example shown, the microelectrodes located at the tissue ablation electrode only pick up a ventricular signal, indicating the tissue ablation catheter is in the ventricle. On the other hand, the ring electrodes pick up both atrial and ventricular signals. Based on these signals, it may be determined that the ablation electrode is likely halfway through the tricuspid valve.

Figure 11:
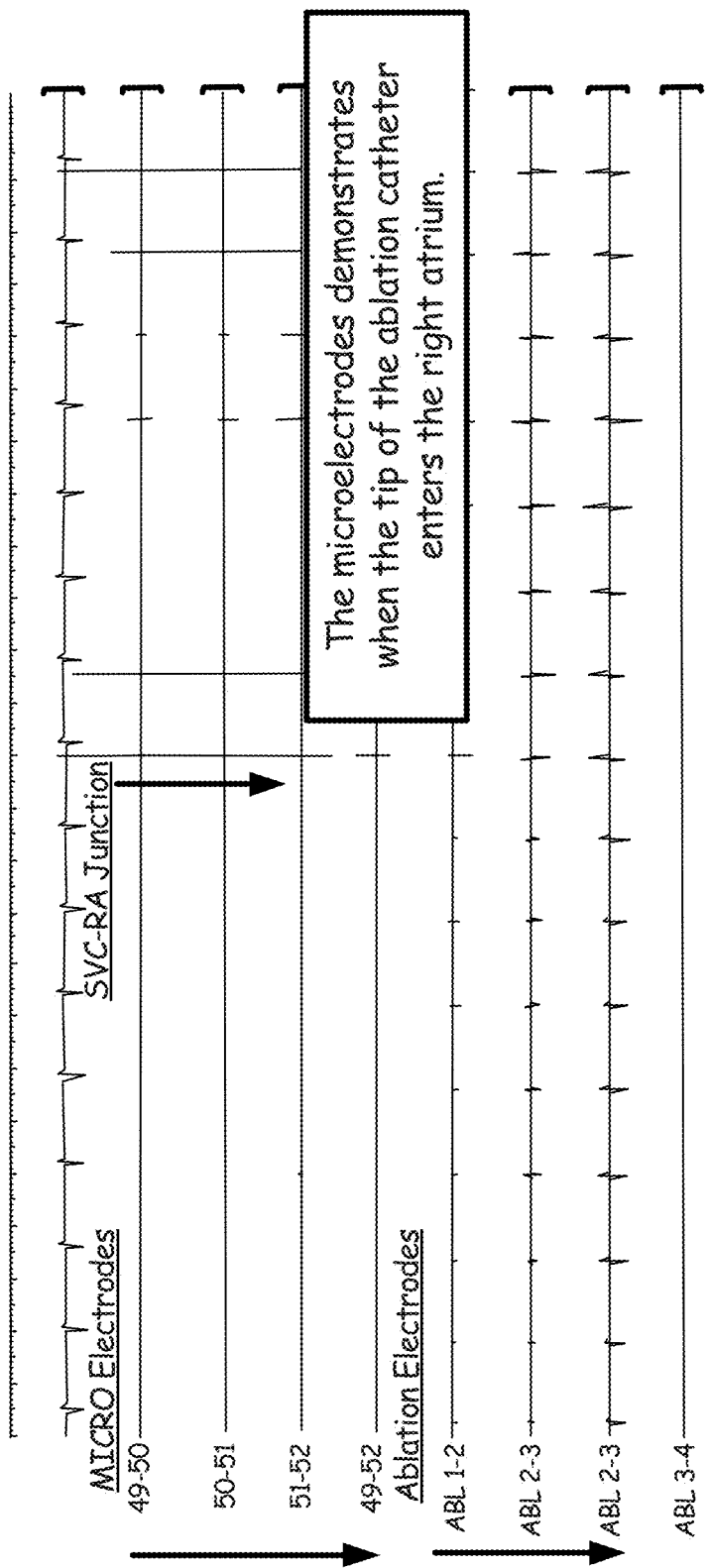
FIG. 11 illustrates an output from a plurality of bipolar microelectrode pairs that can be used by the system of FIG. 1 in a method for discerning different tissue types as the catheter navigates between different cardiac structures.

FIG. 11 illustrates an ECG generated from an output from a plurality of bipolar microelectrode pairs (labeled 49-50, 50-51, 51-52 and 49-52, respectively) that can be used by the system 1 in a method for discerning different tissue types as the catheter navigates between different cardiac structures. In the embodiment shown, the microelectrodes exhibit minimal response as the catheter is located within the superior vena cava. When the catheter exits the superior vena cava and enters the right atrium, the signals generated by the microelectrodes change substantially.

Figure 12:
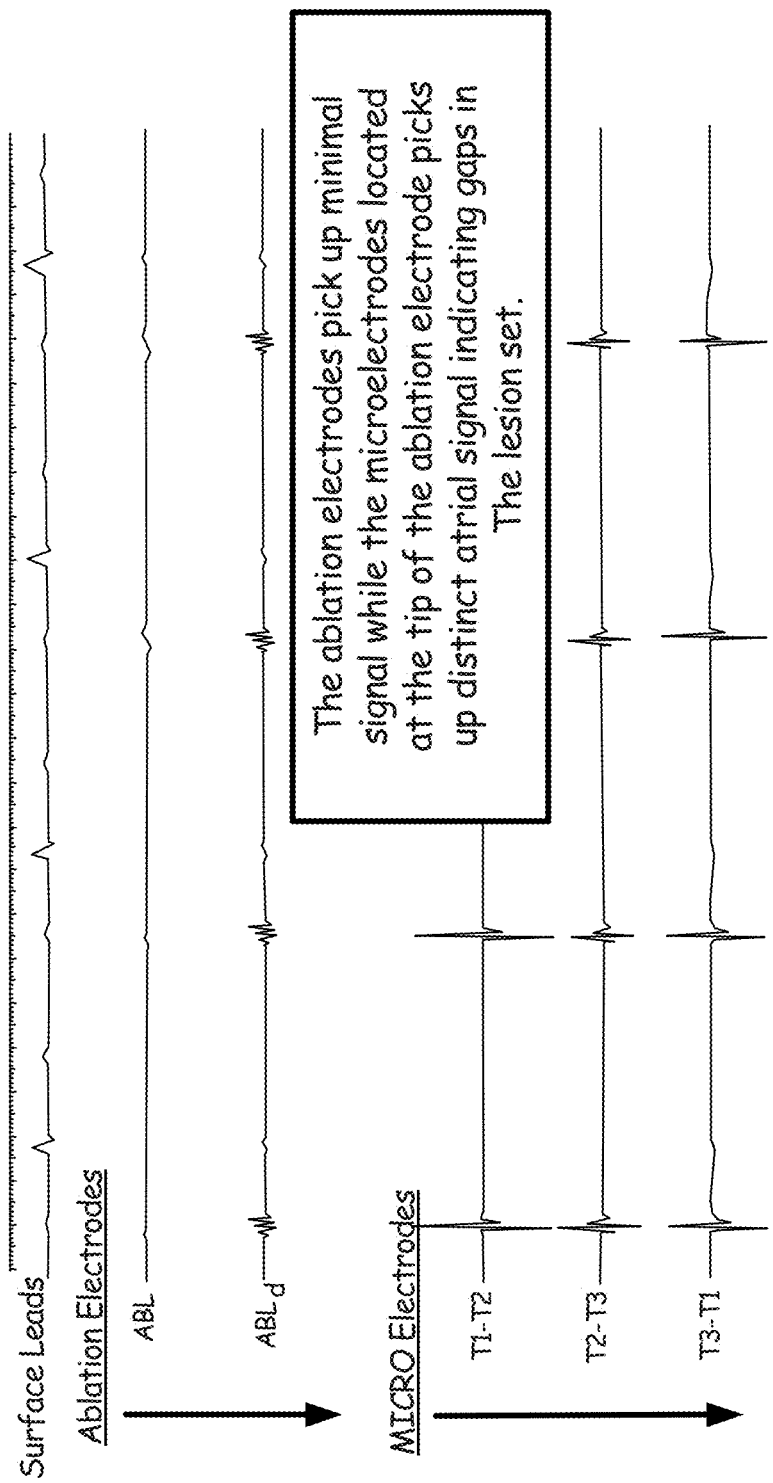
FIG. 12 illustrates an output from a plurality of bipolar microelectrode pairs that can be used by the system of FIG. 1 in a method for identifying gaps in lesion sets based on a comparison of signals between the ablation electrodes and microelectrodes.

FIG. 12 illustrates an ECG generated from an output from a plurality of bipolar microelectrode pairs (labeled T1-T2, T2-T3, T3-T1, respectively) that can be used by the system 1 in a method for identifying gaps in lesion sets. In the example illustrated, the ablation electrodes pick up minimal signals while the microelectrodes located at the tip of the ablation electrode picks up distinct atrial signals, indicating gaps in the lesion set. Thus, in an exemplary method, the mapping processor 4 can identify distinct intrinsic cardiac activation signals in the output signals from the bipolar microelectrode pairs, and thereafter generate an output to a display to identify the corresponding gaps in the lesion sets based on the locations of those bipolar microelectrode pairs. In various embodiments, the mapping processor 4 can further acquire output signals from the ring electrodes 7 (or bipolar pairs defined by two ring electrodes 7 or a ring electrode 7 and the tissue ablation electrode 8) (see FIG. 1), compare the output signals from the bipolar microelectrode pairs to corresponding outputs from the ring electrodes, and use this comparison in identifying the intrinsic activation signals and corresponding gaps in lesion sets.

Figure 13:
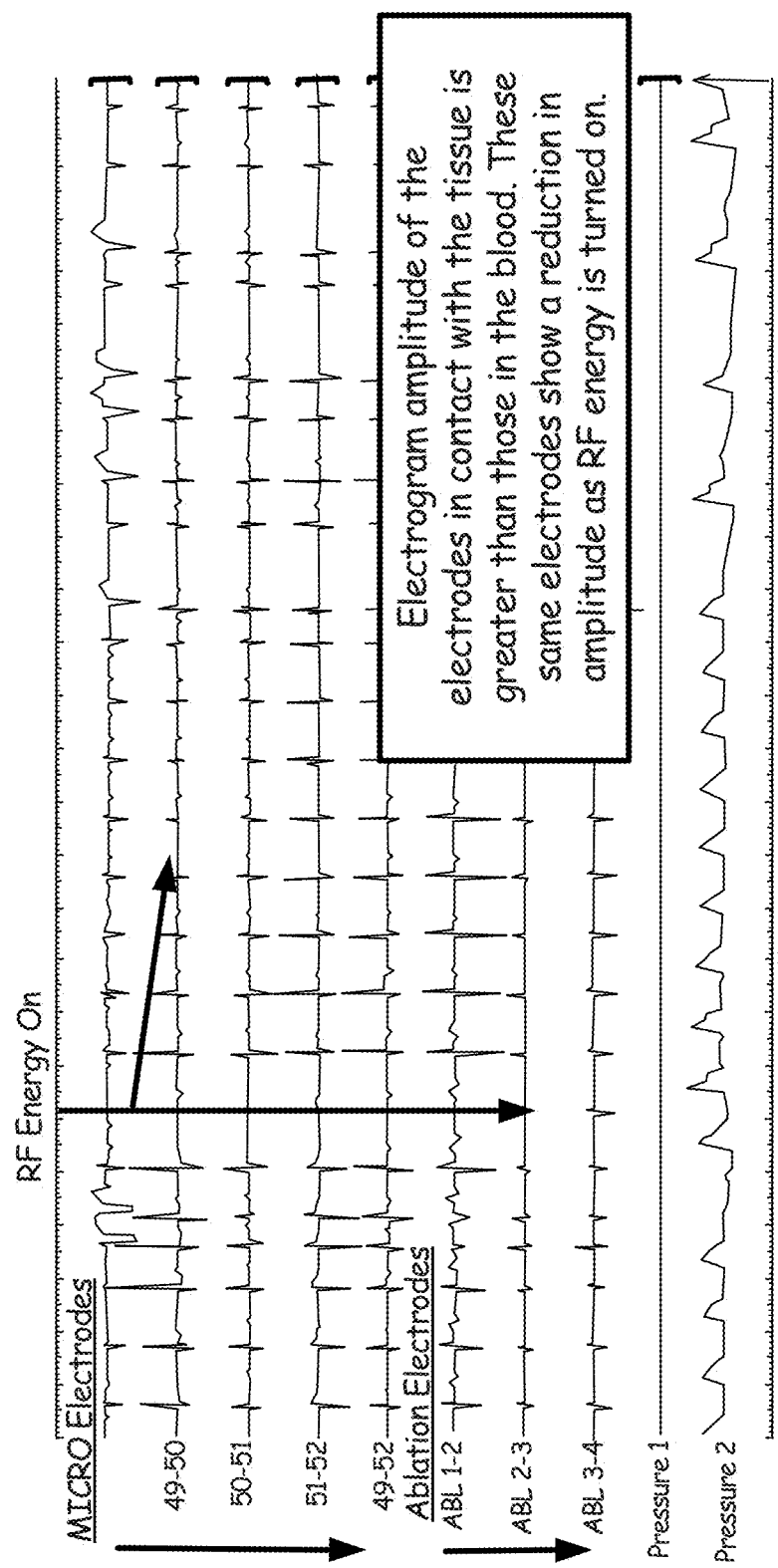
FIG. 13 illustrates an output from a plurality of bipolar microelectrode pairs that can be used by the system of FIG. 1 in a method for assessing electrogram attenuation during ablation.

FIG. 13 illustrates an ECG generated from an output from a plurality of bipolar microelectrode pairs (labeled 49-50, 50-51, 51-52 and 49-52, respectively) that can be used by the system 1 in a method for assessing electrogram attenuation during ablation. In the illustrated example, the electrogram amplitude of the microelectrodes in contact with the tissue is greater than those in the blood. When the RF energy is turned on during ablation, the microelectrodes show a reduction in amplitude.

Figure 14:
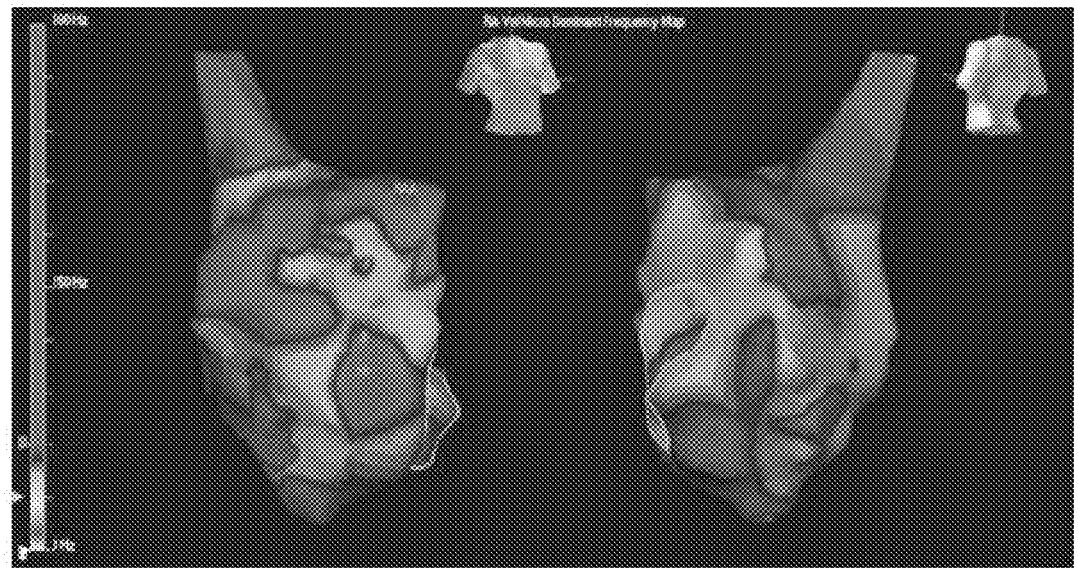
FIGS. 14 and 15 illustrate exemplary electroanatomical maps generated using a catheter including high-resolution microelectrodes according to embodiments of the invention.
Figure 14:
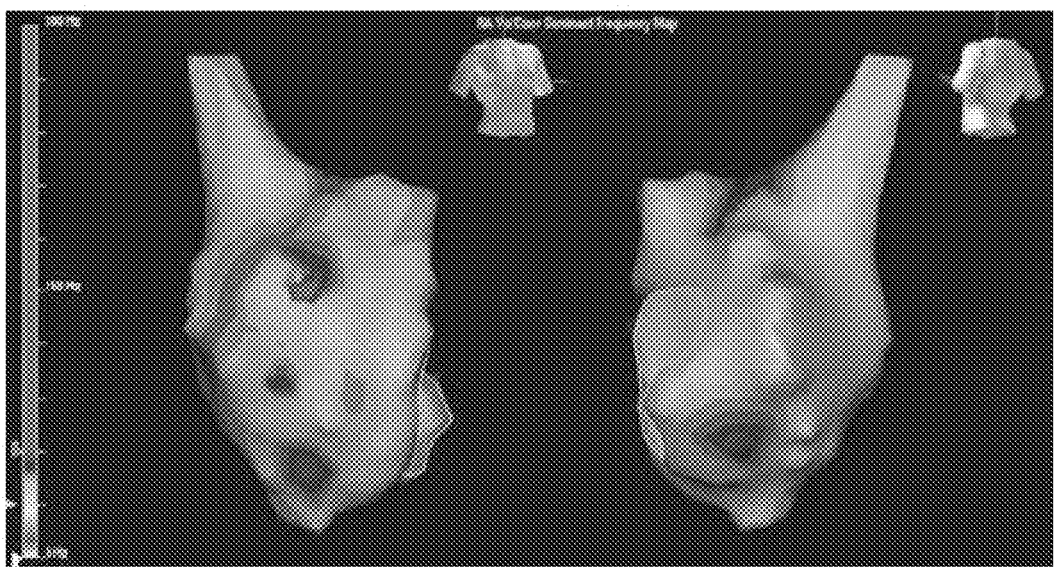
Figure 15:
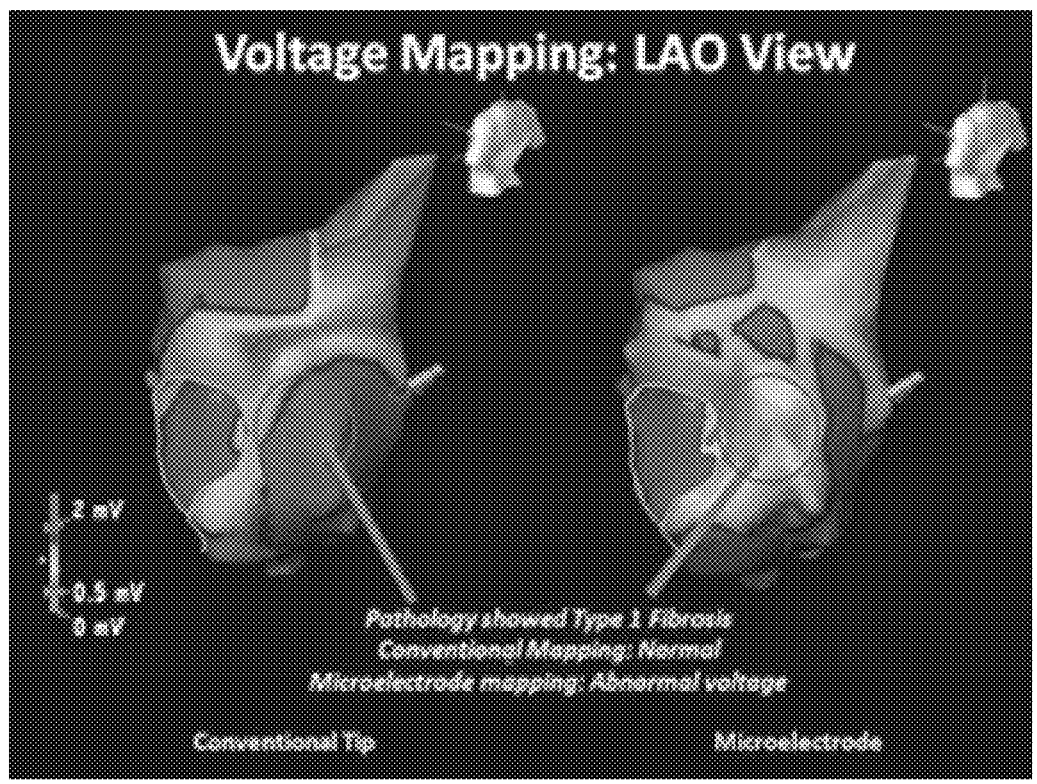

The microelectrode ablation catheters 2, 100 of the various embodiments can also advantageously be integrated with a three-dimensional cardiac mapping system for generating high-resolution electroanatomical maps of the heart for aiding the physician in diagnosing cardiac arrhythmias (e.g., atrial fibrillation), identifying a treatment regime (e.g., ablation procedures such as pulmonary vein isolation) and verifying the sufficiency of the treatment. FIGS. 14 and 15 illustrate exemplary electroanatomical maps 300, 400, 500, 600. In FIG. 14, the map 300 is an exemplary dominant frequency map generated using a conventional ablation catheter such as the catheter 10 in FIG. 2, and the map 400 is an exemplary dominant frequency map generated using the catheter 2 of FIG. 1 or the catheter 100 of FIG. 2 including the plurality of microelectrodes spatially located within the RF ablation electrode. The particularly high signal fidelity provided by the mini-electrodes of the catheter 2, 100 allows the physician to accurately identify abnormal tissue substrates found in fibrotic tissue, thus allowing the physician to more readily discern different tissue types and identify substrates to be ablated (e.g., by analysis of homogeneous or heterogeneous depolarization) than can be accomplished using the conventional ablation catheter 10 of FIG. 2. The advantages provided by the catheter 2, 100 is illustrated in FIG. 15, showing a comparison of electroanatomical maps generated by an exemplary conventional catheter 10 and the catheter 100 of the various embodiments on cardiac tissue confirmed by pathology to exhibit Type 1 fibrosis. As can be seen in FIG. 15 (left image), the map generated using the conventional catheter 10 showed normal voltage distribution within the fibrotic tissue. In contrast, the map generated using the catheter 2, 100 (right image) with the microelectrodes 9, 110 (FIGS. 1, 2 respectively) confirms abnormal voltages in the fibrotic tissue.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An electrophysiology method comprising:
   advancing a distal portion of an ablation catheter intravascularly to a location proximate myocardial tissue within a chamber of a heart, the distal portion of the ablation catheter including:
   a tissue ablation electrode configured to apply ablation energy to the myocardial tissue;
   a plurality of microelectrodes circumferentially distributed about the tissue ablation electrode and electrically isolated therefrom, the plurality of microelectrodes defining a plurality of bipolar microelectrode pairs, each bipolar microelectrode pair configured to generate an output signal based on a cardiac activation signal;
   acquiring the output signals from each of the bipolar microelectrode pairs;
   comparing an amplitude of the output signal from each of the bipolar microelectrode pairs to the amplitudes of the output signals from the other of the plurality of bipolar microelectrode pairs; and
   displaying to a clinician a visual indication of a proximity of the tissue ablation electrode to the myocardial tissue, the visual indication including:
   an indication that the tissue ablation electrode is in contact with the myocardial tissue if, based on the comparison between the amplitudes of the output signals, a difference between the amplitude of any one of the output signals and the amplitude of any one or more of the other output signals exceeds a predetermined threshold; and
   an indication that the tissue ablation electrode is not in contact with the myocardial tissue if, based on the comparison between the amplitudes of the output signals, the difference between the amplitude of any one of the output signals and the amplitude of any one or more of the other output signals does not exceed a predetermined threshold.

2. The method of claim 1, wherein the acquiring and comparing steps are performed by a mapping processor operatively coupled to the microelectrodes.

3. The method of claim 1, wherein the plurality of microelectrodes include three microelectrodes defining first, second and third bipolar microelectrode pairs.

4. The method of claim 3, wherein the three microelectrodes are disposed at the same longitudinal position along the tissue ablation electrode.

5. The method of claim 4, further comprising displaying to the clinician a visual indication of an orientation of the tissue ablation electrode relative to the myocardial tissue based on the amplitudes of the output signals from the first, second and third bipolar microelectrode pairs.

6. The method of claim 5, wherein the ablation catheter further comprises a plurality of irrigation ports in the tissue ablation electrode fluidly and operatively coupled to an irrigation fluid reservoir and pump.

7. The method of claim 1, wherein the ablation catheter further includes a proximal handle having a control element for manipulation by a user, and wherein advancing the distal portion of the ablation catheter includes manipulating the control element to deflect the distal portion for positioning the tissue ablation electrode adjacent to the myocardial tissue.

8. An electrophysiology method comprising:
acquiring signals indicative of bioelectrical cardiac activity from bipolar pairs of microelectrodes of a plurality of microelectrodes, the plurality of microelectrodes circumferentially distributed around a tissue ablation electrode and electrically isolated therefrom, the tissue ablation electrode mounted on a catheter and configured to apply ablation energy to the myocardial tissue;
comparing an amplitude of the signal from each of the bipolar microelectrode pairs to the amplitudes of the signals from the other of the plurality of bipolar microelectrode pairs; and
displaying to a clinician a visual indication of a proximity of the tissue ablation electrode to the myocardial tissue, the visual indication including:
an indication that the tissue ablation electrode is in contact with the myocardial tissue if, based on the comparison between the amplitudes of the output signals, a difference between the amplitude of any one of the output signals and the amplitude of any one or more of the other output signals exceeds a predetermined threshold; and
an indication that the tissue ablation electrode is not in contact with the myocardial tissue if, based on the comparison between the amplitudes of the output signals, the difference between the amplitude of any one of the output signals and the amplitude of any one or more of the other output signals does not exceed a predetermined threshold.

9. The method of claim 8, wherein the acquiring and comparing steps are performed by a mapping processor operatively coupled to the microelectrodes.

10. The method of claim 8, wherein the plurality of microelectrodes include three microelectrodes defining first, second and third bipolar microelectrode pairs.

11. The method of claim 10, wherein the three microelectrodes are disposed at the same longitudinal position along the tissue ablation electrode.

12. The method of claim 11, further comprising displaying to the clinician a visual indication of an orientation of the tissue ablation electrode relative to the myocardial tissue based on the amplitudes of the output signals from the first, second and third bipolar microelectrode pairs.

13. The method of claim 8, wherein the ablation catheter further comprises a plurality of irrigation ports in the tissue ablation electrode fluidly and operatively coupled to an irrigation fluid reservoir and pump.

* * * * *